(12) United States Patent
Aarestad et al.

(10) Patent No.: US 9,820,881 B2
(45) Date of Patent: Nov. 21, 2017

(54) DEVICE AND METHOD FOR OPENING AN AIRWAY

(75) Inventors: Jerome Aarestad, Escondido, CA (US); Richard Rose, Rancho Santa Fe, CA (US); John Nelson, Redlands, CA (US); Donna Palmer, San Diego, CA (US); Paulo Rangel, Carlsbad, CA (US)

(73) Assignee: SOMMETRICS, INC., Vista, CA (US)

( * ) Notice: Subject to any disclaimer, the term of this patent is extended or adjusted under 35 U.S.C. 154(b) by 1430 days.

(21) Appl. No.: 12/993,311

(22) PCT Filed: May 20, 2009

(86) PCT No.: PCT/US2009/044699
§ 371 (c)(1),
(2), (4) Date: Nov. 18, 2010

(87) PCT Pub. No.: WO2009/143259
PCT Pub. Date: Nov. 26, 2009

(65) Prior Publication Data
US 2011/0066086 A1 Mar. 17, 2011

Related U.S. Application Data

(60) Provisional application No. 61/054,799, filed on May 20, 2008.

(51) Int. Cl.
*A61M 15/00* (2006.01)
*A61M 16/00* (2006.01)
(Continued)

(52) U.S. Cl.
CPC ............... *A61F 5/56* (2013.01); *H01P 5/222* (2013.01)

(58) Field of Classification Search
USPC ............ 128/200.24, 202.12, 202.13, 202.16; 601/148–152
See application file for complete search history.

(56) References Cited

U.S. PATENT DOCUMENTS 4,297,999 A * 11/1981 Kitrell ...................... 128/205.16
4,710,165 A 12/1987 McNeil et al.
(Continued)

FOREIGN PATENT DOCUMENTS

| CN | 1527731 A | 9/2004 |
|---|---|---|
| JP | 2004533907 A | 11/2004 |
| WO | 2008076421 A2 | 6/2008 |

OTHER PUBLICATIONS

International Search Report and Written Opinion dated Oct. 19, 2009 issued in PCT/US2009/044699.
(Continued)

*Primary Examiner* — Kristen Matter
(74) *Attorney, Agent, or Firm* — Acuity Law Group, PC; Michael A. Whittaker

(57) ABSTRACT

A device and a method for creating and/or maintaining an obstruction free upper respiratory passages. The device is configured to fit under the chin of a subject adjacent to the subject's neck at an external location corresponding approximately with the subject's internal soft tissue associated with the neck's anterior triangle. The device is capable of exerting negative pressure on the surface of a subject's neck, displacing the soft tissue forward and enlarging the airway.

18 Claims, 21 Drawing Sheets

(51) Int. Cl.
    *A62B 7/00*     (2006.01)
    *A62B 9/00*     (2006.01)
    *A62B 18/00*     (2006.01)
    *A61F 5/56*     (2006.01)
    *H01P 5/22*     (2006.01)

(56) References Cited

U.S. PATENT DOCUMENTS

| | | | | |
|---|---|---|---|---|
| 4,739,755 | A * | 4/1988 | White et al. | 128/206.12 |
| 5,444,786 | A | 8/1995 | Raviv | |
| 6,644,310 | B1 * | 11/2003 | Delache et al. | 128/204.21 |
| 7,182,082 | B2 | 2/2007 | Hoffrichter | |
| 7,762,263 | B2 * | 7/2010 | Aarestad et al. | 128/848 |
| 8,122,891 | B2 * | 2/2012 | Kimani Mwangi | 128/848 |
| 2003/0167018 | A1 * | 9/2003 | Wyckoff | 600/538 |
| 2004/0040563 | A1 * | 3/2004 | Chu et al. | 128/206.21 |
| 2005/0098176 | A1 | 5/2005 | Hoffrichter | |
| 2006/0009697 | A1 | 1/2006 | Banet et al. | |
| 2006/0266369 | A1 | 11/2006 | Atkinson et al. | |
| 2008/0053440 | A1 * | 3/2008 | Farrugia | 128/204.23 |
| 2009/0177124 | A1 * | 7/2009 | Silwa et al. | 601/6 |

OTHER PUBLICATIONS

Stanchina et al., "The influence of white noise on sleep in subjects exposed to ICU noise". Sleep Medicine, 6:423-428, 2005.
Pieters et al., "Acceptance and long-term compliance with nCPAP in patients with obstructive sleep apnoea syndrome", Eur Respir J, 9:939-944, 1996.
Cartwright, "Sleeping Together: A Pilot Study of the Effects of Shared Sleeping on Adherence to CPAP Treatment in Obstructive Sleep Apnea", J. Clin. Sleep Med., 15:123-127, 2008.
"How Vacuum Regulators Work", Equilibar, Inc., http://www.equilibar.com/vacuum-regulator/how-works.asp, Mar. 19, 2013 3:33 PM.
Extended European Search Report and Written Opinion issued in PCT/US2009/044699 dated Jul. 10, 2013.
Office Action issued by CIPO in Canadian patent application No. 2,724,773 dated Aug. 14, 2015.
Office Action and Search Report issued by SIPO in Chinese patent application No. 201510157725.6 dated Aug. 1, 2016.
Extended European Search Report issued in EP 16166941 dated Oct. 20, 2016.
Office Action issued by the JPO in Japanese patent application No. 2014-046420 dated Apr. 7, 2015—incl Engl lang trans.

* cited by examiner

DEVICE AND METHOD FOR OPENING AN AIRWAY

This application is filed under 35 U.S.C. §371 as the U.S. national phase of International Application No. PCT/US2009/044699, filed 20 May 2009, which designated the U.S. and claims the benefit of priority to U.S. Provisional Application Ser. No. 61/054,799, filed May 20, 2008, which is hereby incorporated by reference in its entirety, including all tables, figures, and claims.

FIELD OF THE INVENTION

The present invention relates generally to medical devices. More particularly, the present invention relates to a device for creating improving patency in the upper respiratory passage.

BACKGROUND OF THE INVENTION

The following discussion of the background of the invention is merely provided to aid the reader in understanding the invention and is not admitted to describe or constitute prior art to the present invention.

Obstruction of the upper respiratory passages (referring to the nasopharynx, oropharynx, laryngopharynx, and larynx) can occur at any age. Those at risk for obstruction of some portion of the upper respiratory passages include persons with sleep apnea, those with airway tumors or foreign bodies such as aspirated food, and those with inflammatory or traumatic damage to the upper respiratory passages, which results in obstruction of the airway.

The medical sequalae of upper respiratory passage obstruction can be devastating: an inability to effectively ventilate the lungs rapidly produces hypoxemia, a generalized condition of lowered blood oxygen. If left uncorrected, hypoxemia leads to serious end organ injury such as stroke and myocardial infarction (heart attack), and may have a lethal outcome.

Snoring is a common chronic medical problem that is associated with episodic partial upper respiratory passage obstruction during sleep. Snoring afflicts millions of people worldwide. Snoring can lead to chronic fatigue that follows sleep deprivation and is considered by many to be a serious medical problem. The sound of snoring is produced by turbulent air-flow moving through an area of upper respiratory passages obstruction that produces resonant vibrations in the soft tissues, typically of the oropharynx.

A percentage of those who snore also suffer from sleep apnea, another frequent and serious medical condition associated with episodic upper respiratory passage obstruction. In the most common type of sleep apnea, obstructive sleep apnea (OSA), an afflicted individual sustains numerous episodes of apnea, or complete, and often prolonged cessation of breathing. Severe cases may have 100 or more apnea events per hour of sleep. OSA results in nocturnal hypoxemia, and leads to cognitive impairment, daytime somnolence, hypertension, increased risk of stroke and myocardial infarction, and insulin resistant diabetes mellitus. Untreated, OSA may result in premature death.

OSA is caused by occlusion of a portion of the upper respiratory passages, usually at the level of the orphharynx, during sleep due to either alteration in the mechanical properties of the tissues in or near the upper respiratory passages, and/or to disturbances in neuromuscular control over airway caliber. The immediate factor leading to collapse in the upper airway is a negative pressure in the airway that exceeds the ability of muscles in the airway to maintain an open state. Alterations in the mechanical properties of the upper respiratory passages, which predispose to collapse of the upper respiratory passages during sleep, may be caused by anatomical conditions such as large tonsils, or may be idiopathic. A variety of medical interventions have been shown to improve the mechanical properties of the upper respiratory passages and reduce sleep related airway closure. These include remodeling surgeries, medical devices that re-position the mandible, and continuous positive airway pressure (CPAP).

Unfortunately, all current treatments produce results that are far from optimal. Surgery and re-positioning devices are effective in only a minority of OSA patients, and the responders cannot be identified with certainty prior to initiating treatment. As a result, many people are subjected to painful and expensive procedures without benefit. On the other hand, CPAP is effective in the majority of OSA patients; however, the treatment is uncomfortable and not well tolerated during long-term use. A substantial number of patients given CPAP discontinue therapy within the first year after initiation.

CPAP works by delivering air at pressures above ambient pressure to the upper respiratory passages during sleep. Application of positive pressure to the upper respiratory passages acts as a "stint" and can retard the tendency of the upper respiratory passages to collapse during certain stages of sleep in OSA patients. In order to deliver higher than ambient pressures to the upper respiratory passages, the patient must wear a tight fitting mask covering the mouth and/or nose. This mask is connected to an air supply tube, and a variable pressure air pump. An additional component can be added which humidifies the air, to avoid desiccation of the upper respiratory passages during treatment. There are multiple sources of patient dissatisfaction with CPAP including difficulty of exhaling against the delivered air pressure, an uncomfortable face mask which may provoke feelings of claustrophobia, the noise of the air pump and the moisture of the humidification system. Additionally, the effects of device noise, mask exhaust, and user discomfort can substantially disrupt sleep patterns of a user's spouse or companion. Also, some CPAP units are not easily portable and limit patients' ability to travel.

Therefore, there is a pressing medical need to develop a means of ameliorating obstruction of the upper respiratory passages, which is both highly effective and well tolerated during chronic use.

SUMMARY OF THE INVENTION

The present invention provides devices and methods for assisting in improving the patency of an upper respiratory passage of an individual.

In a first aspect of the invention, a therapy appliance is provided that has a surface which is configured to enclose an external area of the throat (the term "throat" as used herein referring to the anterior portion of the neck extending approximately from the chin to the top of the sternum and laterally to a point posterior to the external jugular vein) overlying a portion of the upper respiratory passage, thereby providing a chamber (e.g., a hollow space filled with air molecules) lying between the surface and the throat. The appliance is configured to fit under the chin of a subject adjacent to the subject's throat at an external location corresponding approximately with the subject's internal soft tissue associated with the neck's anterior triangle. The skin area enclosed by the appliance preferably comprises between about 32.90 cm² and about 210.58 cm² of this anterior triangle. The therapy appliance has a peripheral contact surface with the user's skin (an edge or lip) that forms a seal on the wearer's skin to enclose the internal chamber, with the internal appliance surface facing but separated from the user's skin.

The therapy appliance is operably connected to an air pump which is configured to produce a partial vacuum in this chamber by removal of at least a portion of the gas molecules in this volume. Although the therapy appliance may have some ability to flex, the appliance is configured to be less compliant than the soft tissues of the throat, such that this partial vacuum will tend to draw the soft tissues outwards into the chamber, thus helping to open the breathing passages within the throat underlying these soft tissues. The air pump is designed to provide extremely quiet operation and with minimal vibration. Preferably, the pump delivers an operating partial vacuum at a volume of less than 40 dB SPL (SPL=sound pressure level), more preferably less than 30 dB SPL, and most preferably less than 25 dB SPL. Suitable air pumps are described in detail hereinafter.

The term "seal" as used in this context is not meant to imply that a perfect seal is formed between the appliance and the user's skin. Rather, a certain amount of leakage at the seal may be tolerated so long as the desired partial vacuum can be achieved. Preferred operational vacuum levels are in a range of between about 7.6 cm to about 61 cm of water. Preferred forces applied to the user's neck tissues in order to assist in opening the upper respiratory passages are in a range of about 0.5 kilogram to about 6.68 kilograms. The chamber enclosed by the mask provides a finite volume which must be evacuated to deliver the desired partial vacuum level. Once generated, the partial vacuum will decay at a rate which is primarily controlled by leakage of air into the chamber past this seal. In certain embodiments, the mask encloses a volume of between 0.5 and 12 in³. Preferably, the leakage is no more than between about 0.005 and 0.5 in³/min, and most preferably between about 0.01 and 0.1 in³/min.

The air pump may provide for continuous operation in order to compensate for this decay in the partial vacuum. In such embodiments, the partial vacuum generated by a continuously running air pump may be controlled to prevent too great a partial vacuum being generated, for example by providing a valve which limits pump-generated vacuum levels to a desired range by opening should the desired vacuum level be exceeded. The valve may be mounted through a port in the therapy appliance such that it is easily replaceable. Selection of a partial vacuum level may be achieved by simply selecting a valve which opens at a desired vacuum level and inserting that valve into the port.

Provided that the seal is adequate, however, leakage into the appliance may be maintained at a sufficiently low rate that constant pumping is not required. Thus, once the initial working partial vacuum has been achieved, the air pump may advantageously provide discontinuous operation, meaning that the pump "cycles on" only as needed to counteract decay of the partial vacuum. In those embodiments where the vacuum source is powered by one or more batteries rather than from a mains power circuit, discontinuous operation of the pump can advantageously conserve battery life.

Particularly preferred air pumps would be configured to provide a "dual mode" pumping profile, wherein the pump provides an initial high rate of pumping to generate working partial vacuum, followed by a "quiet mode" in which the air pump operates very slowly. In these preferred embodiments, a preferred high rate mode is between 1 and 25 in³/min, most preferably between 5 and 15 in³/min, and a preferred quiet mode is set at a rate that compensates for leakage of air into the mask. If that leakage is between 0.005 and 0.5 in³/min, the quiet mode rate is also between 0.005 and 0.5 in³/min. A preferred quiet mode rate is between 0.01 and 0.1 in³/min. The on/off cycling of the air pump in the quiet mode is preferably controlled by a vacuum or pressure sensor which monitors the chamber partial vacuum and controls air pump activity accordingly.

Such sensors may also be advantageously used to determine if a seal has been dislodged such that the therapy appliance can no longer achieve the desired partial vacuum. Because the volume enclosed by the appliance and the user's skin is approximately known, the time to achieve the partial vacuum can be calculated. If it is determined that the partial vacuum has not been achieved in some appropriate time, the vacuum source can be deactivated, and optionally an alarm condition indicated. Suitable alarms can include visual (e.g., a light), auditory (e.g., a tone), and or tactile (e.g., vibration) indicators.

The seal to the wearer's skin may be achieved in a variety of ways. For example, the partial vacuum may act to hold the appliance to the wearer; the sealing surface of the appliance may include an adhesive surface; the sealing surface may receive a liquid or gel material to improve sealing; the sealing surface of the appliance may comprise a material having a durometer of between 15 and 30, providing a soft seal that flows into undulations of the skin; the appliance may include a strap to hold the appliance to the wearer, etc. In certain embodiments, one or more continuous ridges run approximately parallel to the periphery of the sealing surface. Such ridges can impart high local contact loads on the skin, thereby establishing a barrier to leakage that naturally occurs when sealing an uneven surface like the skin.

Because the contact surface of the appliance applies compressive pressure to the user's skin due to the forces generated by the partial vacuum, the capillaries, arterioles, and venules in the skin underlying the edge or lip may collapse under high loads and/or prolonged use. Thus, the contact surface and/or seal structure is preferably configured to distribute force loads across a sufficient skin area to minimize peak localized contact pressures, commonly referred to as "hot spots." Preferably, no compressive pressure along the contact surface with the user's skin exceeds 60 mm Hg, preferably 40 mm Hg, more preferably 30 mm Hg, and most preferably 25 mm Hg.

In certain embodiments, the partial vacuum can be cycled during at least part of the therapy period to a lower level. This can provide times of reduced contact pressures which improve venous flow by reducing appliance-generated disruptions in that flow. This cycling can advantageously be synchronized to coincide with the inspiration/expiration cycle such that the partial vacuum is increased during inspiration. Alternatively, or in addition, this cycling can be timed to coincide with the onset of an apnea or snoring event such that the partial vacuum is increased during the event, but decreased in the absence of an event. In these embodiments, sensor circuitry either integral to the appliance or external to the appliance can be used to sense inspiration/expiration or apnea events.

Numerous sensor technologies designed to respond to sound, light, temperature, humidity, and other variables are known in the art. Examples of such sensors include thermistors to measure respiration airflow temperature, acoustic sensors, oximeters, vibration sensors, etc., which have found use in sensing respiratory cycles and apnea or snoring events. The sensor is preferably operably coupled to a microprocessor for signal processing, such as calculating normal respiration cycles, peak-to-peak amplitude for each consecutive breath cycle, and other parameters of the respiration pattern, and the microprocessor is further operably coupled to control circuitry for controlling a connection between the vacuum source and the enclosed space, and/or controlling the vacuum source itself.

The therapy appliance of the present invention must be configured to be of sufficient structural integrity that it does not collapse onto the throat under the desired partial vacuum condition in order to maintain a chamber between the surface and the throat. The appliance may be configured as a single structural unit of sufficient integrity to meet this requirement. Suitable materials such as silicone, urethane or rubber having a sufficient durometer to withstand the required vacuum levels may be used. Preferred durometers are in the range of 40 to 50. Alternatively, the appliance may be made of a flexible material that is attached to a skeletal superstructure overlying the appliance, where the skeletal structure provides additional support to withstand the partial vacuum. The appliance can attach to the skeletal structure, for example with straps, snaps, hook-and-loop fasteners, etc. In these embodiments, the appliance can be made as a single use or limited use disposable. To adjust to a user's anatomy, the superstructure may be made of a material that is sufficiently compliant as to be deformable while still maintaining integrity to the partial vacuum. Likewise, multiple sizes of the superstructure may be provided to further customize to the user.

In certain embodiments, the air pump is a separate unit from the therapy appliance, in which case an inlet is provided on the appliance to operably connect the enclosed chamber to the air pump. In these embodiments, a tube or other conduit connecting the appliance to the air pump may be provided. In preferred embodiments, however, the therapy appliance attaches directly to, and is supported on the user's body by, a physical connection to the appliance. Thus, in preferred embodiments, the therapy appliance is configured to wearably attach the air pump to the user such that it is supported on the therapy appliance in order to provide for ambulatory movement of the user during use of the appliance. By "ambulatory" is meant that the therapy appliance need not require connection to any elements not supported on the user's body during use. As such, the user may move freely while the appliance is in use. In certain embodiments, the air pump is provided as an integral part of the appliance. In these embodiments, a vacuum tube is preferably not used in order to increase the compactness of design. Alternatively, the air pump is provided as part of the appliance by attachment to, for example, a strap which positions the air pump on the side or back of the neck.

In its simplest form, the air pump of the ambulatory therapy appliance may operate continuously in conjunction with a replaceable valve used to select an operating partial vacuum level, as discussed above. In various embodiments, however, the ambulatory therapy appliance may comprise, in addition to an integrated air pump, one or more of the following: a battery power source; a microcontroller operably connected to a vacuum or pressure sensor to determine the partial vacuum level within the chamber and control air pump function accordingly; motor control circuitry operably connected to the microcontroller to drive the air pump in response to signals from the microcontroller; an input device to input a desired partial vacuum level to the microcontroller. Collectively, two or more, and preferably all, of these elements may be provided in a single hardware module which, like the air pump, is supported on the therapy appliance in order to provide for ambulatory movement of the user during use of the appliance.

In certain embodiments, a structure, referred to herein as "a buffering component," is provided as part of the therapy appliances described herein, in order to buffer swings in the partial vacuum caused by user movement.

When wearing the therapy appliances of the present invention, a seemingly simple movement such as coughing or swallowing can increase the volume enclosed by the therapy appliance by about 20% or more due to displacement of the throat. Because of the ideal gas law, this increase in enclosed volume causes an equivalent percentage increase in the partial vacuum within the therapy appliance chamber. Moreover, because the partial vacuum is not held at a constant value during use, this increase in volume is perceived by the user as a sudden increase in the pressure exerted on the tissues of the throat, an increase in pressure at the contact surfaces of the appliance on the throat, etc., all of which can cause an increase in discomfort to the wearer and arousal from sleep. To counteract this effect, at least part of the appliance surface enclosing the chamber may be configured to provide a "spring" effect that moves to at least partially counteract the movement-induced volume change.

In certain embodiments, this buffering component of the appliance is provided as a displaceable diaphragm attached to a spring. The spring is designed to compress (or expand, depending on which side of the diaphragm is attached to the spring) when the force exerted on the diaphragm by the partial vacuum within the chamber is increased by body movement. As the anatomy of the throat displaces during movements such as swallowing or coughing, this acts to increase the enclosed volume of the therapy appliance. An inward movement of the diaphragm would act to partially or nearly completely counter that volume increase. Then, as the throat returns to its original condition, the spring attached to the diaphragm would act to return the diaphragm to its original position.

Alternative embodiments of the buffering component of the appliance will be readily apparent to those of skill in the art. In preferred embodiments, the appliance contains a structural region made of a resilient "memory shaped" material that flexes inward during body movement to partially or completely counter a volume increase, but that quickly returns to its original shape as the air pressure within the therapy appliance returns to its original state. In a particularly preferred embodiment, this memory shaped material is configured as a resilient pleated (or bellows-like) region which is able to move inward and outward by compression and expansion of the pleats. Such an embodiment may be thought of as akin to a modern speaker, in which a relatively rigid central cone is connected at its periphery to a flexible surround which provides for reciprocating movement. As described herein, the rigidity in the "structural" or "non-buffering" regions or zones of the appliance may be provided by the character of the material itself, by contouring the material into struts, by including a supportive brace or reinforcing member of some sort, by some combination of these features, or by other means. An example of such a preferred embodiment is described hereinafter.

In an alternative particularly preferred embodiment, this memory shaped material is configured as a central region or zone of increased flexibility which is connected at its periphery to the "structural" or "non-buffering" regions or zones of the appliance. This region of increased flexibility allows a portion of the appliance to deform inward during movement, thereby partially or completely countering a volume increase, but then to quickly return to its original shape as the air pressure within the therapy appliance returns to its original state. The increased flexibility may be provided by introducing a region that is reduced in thickness relative to the structural regions of the therapy appliance, by introducing a region formed of a material that is reduced in durometer relative to the material forming the structural regions of the therapy appliance, or by a combination of such methods.

In still another particularly preferred embodiment, the therapy appliance may comprise a flexible material that is attached to a skeletal superstructure overlying the appliance, and a portion of the superstructure provides increased flexibility relative to the "structural" or "non-buffering" regions or zones of the superstructure. This region of increased flexibility again allows a portion of the appliance to deform inward during movement, thereby partially or completely countering a volume increase, but then to quickly return to its original shape as the air pressure within the therapy appliance returns to its original state.

Preferably, the buffering component of the appliance partially or nearly totally mitigates the movement-induced increase in the force exerted on the tissues of the throat. In preferred embodiments, the peak increase in the partial vacuum created by coughing or swallowing is reduced by at least 25%, more preferably at least 50%, still more preferably at least 60%, yet more preferably at least 70%, and most preferably between 70% and 90% or more. These ratios are the differential volume calculated by dividing the buffered volume by the movement-induced volume. The term "movement-induced volume" as used herein refers to the volume by which the chamber enclosed by the appliance is increased due to user swallowing, when an appliance lacking a buffering component is mated to the user and an effective partial vacuum is provided in the chamber. The term "buffered volume" as used herein refers to the volume by which the chamber enclosed by the appliance is increased due to user swallowing, divided by the increase in volume due to user swallowing of a similar appliance which lacks a buffering component.

The various elements described herein may be used in any combination in conjunction with a therapy apparatus. For example, (i) the therapy apparatus having a buffering component may be used in conjunction with a continuous vacuum source, or with the discontinuous pumps described herein; (ii) the ambulatory therapy apparatus described herein may or may not comprise a buffering component; (iii) the embodiments of (i) or (ii) may further comprise a hardware module; (iv) the embodiments of (i), (ii) or (iii) may further comprise one or more sensors; (v) the embodiments of any one of (i)-(iv) may be configured to distribute force loads across a sufficient skin area such that no pressure along the contact surface with the user's skin exceeds 60 mm Hg; (vi) the embodiments of any one of (i)-(v) may cycle the partial vacuum such that the partial vacuum is increased during inspiration; etc.

Additionally, the therapy appliance may further comprise one or more of the following elements: a cord for mains power connection; battery charging circuitry; "white noise" circuitry; "noise cancellation" circuitry; data collection circuitry; and/or data transmission circuitry. These embodiments are described in more detail hereinafter.

In a related aspect of the invention, a method is provided for application of a partial vacuum to the external soft tissues of the throat surrounding a portion of upper respiratory passages of a subject. In these methods, a therapeutic appliance as described herein is attached to the subject, and a partial vacuum is created in a chamber formed between the inner surface of the appliance and the skin surface of the subject's throat, wherein the partial vacuum is sufficient to draw the soft tissues of the throat outwards into the chamber. The result of drawing the soft tissues outward in this manner is maintaining or increasing opening of the airway. In preferred embodiments, the subject is selected for treatment based on a diagnosis of obstructive sleep apnea and/or snoring.

In another related aspect of the invention, a method is provided for manufacture of a therapeutic appliance for application of a partial vacuum to the external soft tissues of the throat surrounding a portion of the upper respiratory passages of a subject. In these methods, an appliance is formed having an internal surface; a peripheral contact surface configured to mate with the user's skin to thereby enclose a chamber; and an air pump is operably connected to the chamber to produce a partial vacuum therein when the appliance is in use.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

The present invention and the various features and advantageous details thereof are explained more fully with reference to the non-limiting embodiments that are illustrated in the accompanying drawings and detailed in the following description. It should be noted that the features illustrated in the drawings are not necessarily drawn to scale. Descriptions of well-known components and processing techniques are omitted so as to not unnecessarily obscure the present invention. The examples used herein are intended merely to facilitate an understanding of ways in which the invention may be practiced and to further enable those of skill in the art to practice the invention. Accordingly, the examples should not be construed as limiting the scope of the invention. In the drawings, like reference numerals designate corresponding parts throughout the several views.

DETAILED DESCRIPTION

Figure 1:
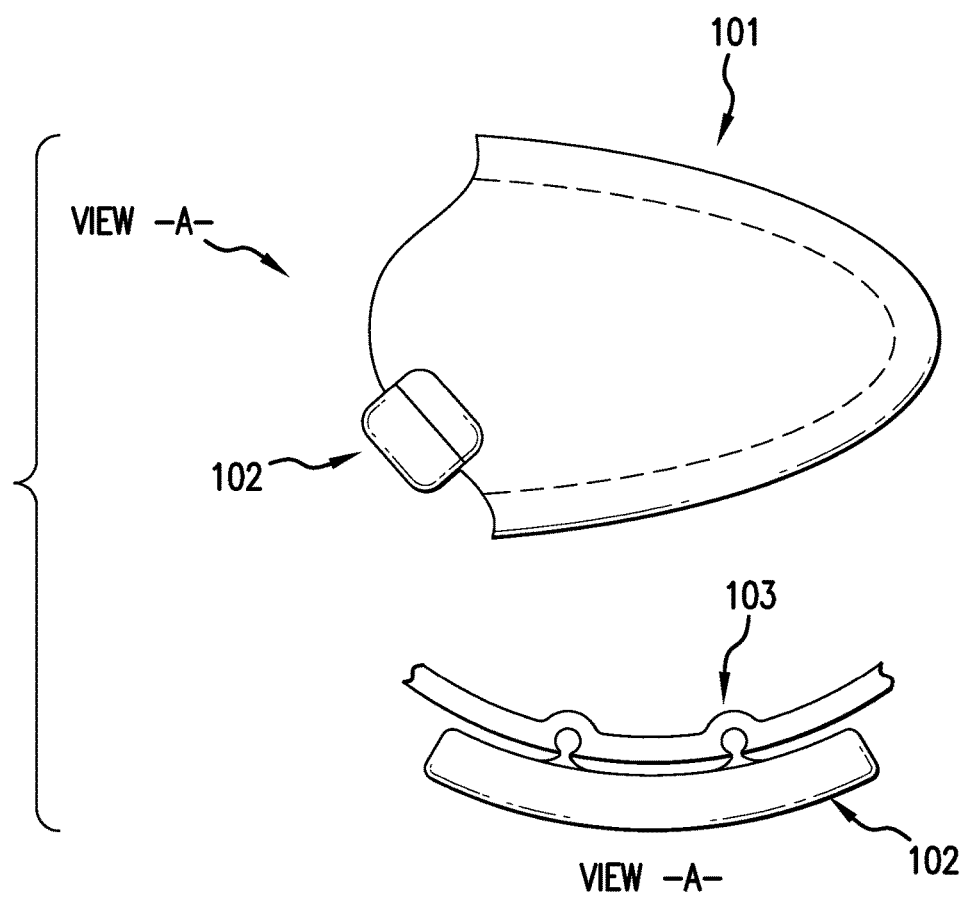
FIG. 1 depicts a side view (top) and cross-sectional view (View A) of an exemplary therapy appliance carrying an electronics and mechanical module.

External Therapy Appliances for Relieving Airway Obstruction

The minimal design for a therapy appliance for relieving airway obstruction is a structure configured to provide a space-filled chamber between an inner surface of the appliance and the skin of the throat when mated to the user, where the structure is sufficiently rigid to withstand a desired partial vacuum created within the space; and to provide a peripheral rim that seals to the skin of the user in order to enclose the chamber. Once created within the chamber, a sufficient partial vacuum acts to move the soft tissues overlying a portion of the upper respiratory passages into the space, thereby increasing the patency of the respiratory passage.

U.S. patent application Ser. No. 12/002,515, filed Dec. 17, 2007, which is hereby incorporated by reference in its entirety including all tables, figures and claims, describes a therapy appliance for relieving airway obstruction. As described therein, a device is configured to fit under the chin of a user at an external location corresponding to the soft tissues overlying the upper respiratory passages of the neck. A vacuum source connected by a tube creates a negative pressure over the airways in order to assist in opening the airway. A vacuum in the range of about 7.62 to about 60.96 cm $H_2O$ is applied to a skin surface area of about 32.90 $cm^2$ to about 210.58 $cm^2$ in order to apply the desired amount of force to these soft tissues. The therapy appliances are described as having particular application to treatment of snoring and obstructive sleep apnea.

These external therapy appliances have typically required a port connecting the enclosed space to an external vacuum source and power supply in order to achieve the desired therapeutic benefit for an entire treatment period (e.g., overnight). As these devices are typically intended for use during sleep, this "tethered" design can be disruptive to the user. In addition, noise and vibration from the appliance and its associated hardware can further disrupt sleep for both the user, as well as other nearby individuals.

A. The Therapy Appliance

The therapy appliance of the present invention comprises a structural member that provides a chamber between an inner surface of the appliance and the skin of the throat, where the structure is sufficiently rigid to withstand the required partial vacuum created within the space, and a peripheral rim that seals to the skin of the user in order to enclose the space. The vessel may be formed, molded, or fabricated from any material or combination of materials. Non-limiting examples of such materials suitable for constructing the therapy appliance include plastics, metals, natural fabrics, synthetic fabrics, and the like. The appliance may also be constructed from a material having resilient memory such as silicone, rubber, or urethane.

The only limitations on material(s) used for manufacture of the therapy appliance is that the appliance must be nontoxic (or "biocompatible," as it is in contact with the skin), and must be sufficiently rigid to maintain the space while carrying the desired partial vacuum load. The durometer is a unit of a material's resistance to indentation. The durometer of common materials is provided in the following table:

| Material | Durometer |
| --- | --- |
| Bicycle gel seat | 15-30 |
| Chewing Gum | 20 |
| Sorbothane | 40 |
| Rubber band | 25 |
| Door seal | 55 |
| Automotive tire tread | 70 |
| Soft skateboard wheel | 75 |
| Hydraulic O-Rings | 70-90 |
| Hard skateboard wheel | 98 |
| Ebonite Rubber | 100 |
| Solid truck tires | 50 |
| Hard Hat | 75 |

The term "structural regions" as applied to the therapy appliance refers to those portions of the appliance intended to carry the vacuum load without substantial flex as the vacuum is increased. This is in contrast to the buffering component, which is by definition intended to flex as the vacuum increases past some desired level. In those embodiments where a flexible membrane is used in conjunction with a superstructure, the structural regions of the therapy appliance are all or a portion of the superstructure.

The structural regions of the therapy appliance may be constructed of silicone rubber having a durometer on the order of 50 to 60 and a thickness of about 0.10-0.25 in. The skilled artisan will understand that as the thickness of the material is increased or decreased, the required durometer may be somewhat different.

The connection to the air pump may be made through a tube or other extended connector which provides access to the chamber formed by the therapy appliance. It may be preferable that the vacuum source mates directly with the chamber to minimize the volume of air that must be extracted by the air pump and to improve the compactness of the design. A port in the appliance can mate with a corresponding connector on the air pump to provide the necessary communication between the source and the chamber in a fashion similar to that of a Luer type fitting.

In preferred embodiments, the appliance acts as support for positioning the necessary electronic and mechanical module(s) on the user. In particularly preferred embodiments, one or more modules are centrally located on the lower front of the appliance as depicted in FIG. 1. This configuration locates the additional weight of the module(s) 102 on the appliance 101 so as to position them close to the neck, which minimizes the tendency for dislodging of the appliance at low vacuum levels. While the module(s) may also be located on a side of the appliance, such a configuration may interfere with sleeping. In alternative embodiments, one or more of the modules may be physically separated from the appliance and worn by the user, for example, under the arm. Such configurations, while less compact, still retain the ambulatory nature of the design.

Figure 2:
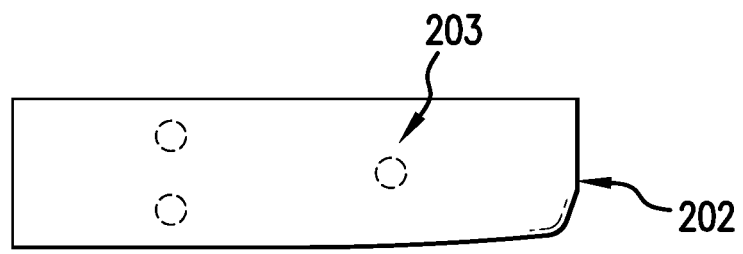
FIG. 2 depicts exemplary fastener locations for attaching the electronics and mechanical module to the therapy appliance.

In FIGS. 1 and 2, the electronic and mechanical module 102 and 202 is depicted as being held externally to the appliance, in this case with a three point snap 103 and 203, although other fastener systems known to those of skill in the art can be used. Such a mounting configuration can isolate the therapy appliance from the physical rigidness of the electronic and mechanical module(s), thereby allowing the appliance to flex and comply with the anatomy of each user. This external mounting can also minimize vibrations generated within the electronic and mechanical module(s) being carried into the appliance. Advantageously, one of the snap points can provide the port access through the appliance by which the vacuum module evacuates air from the enclosed chamber. In addition, the module may be positioned to physically cover, and thereby protect, the buffering component.

Figure 5:
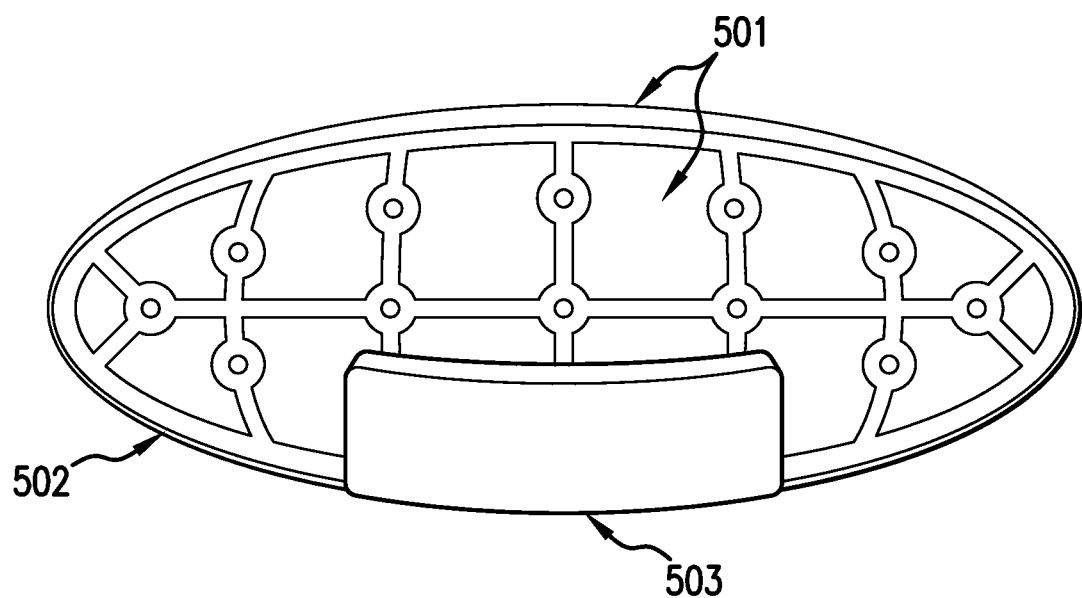
FIG. 5 depicts an exemplary therapy appliance carrying an electronics and mechanical module, where the appliance and module are supported on a superstructure.
Figure 6:
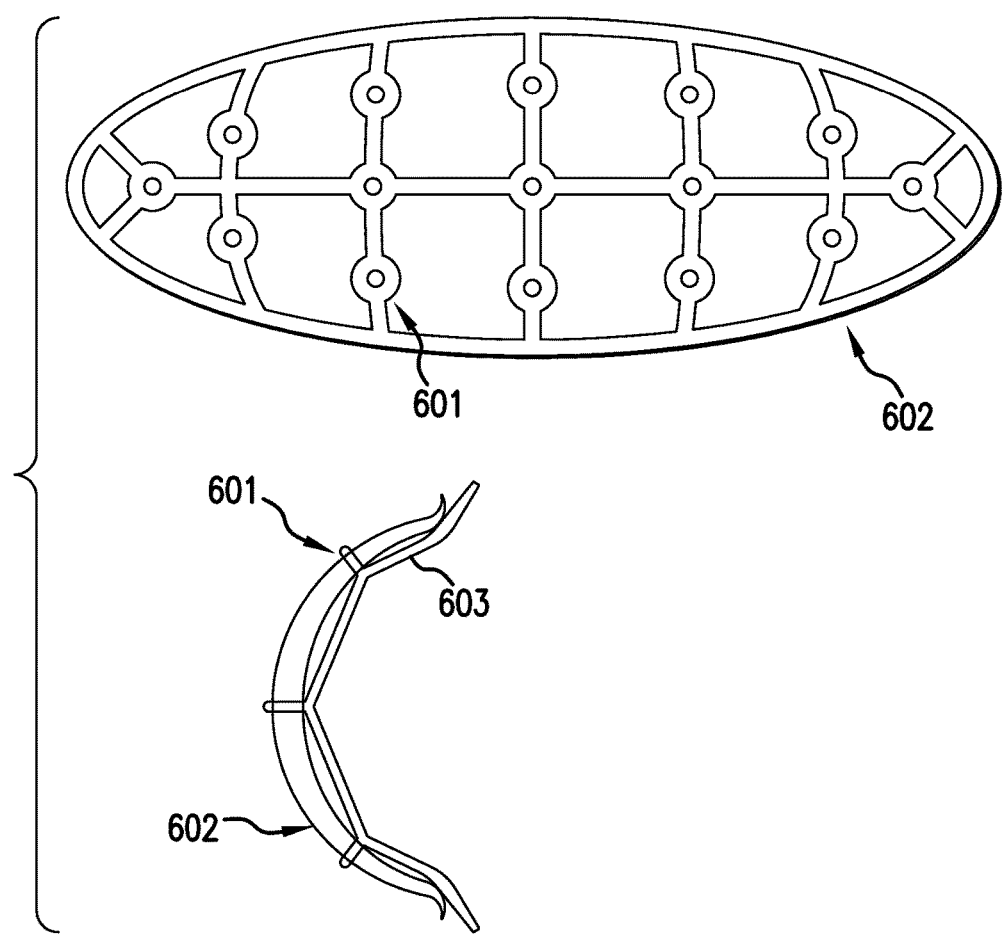
FIG. 6 depicts a frontal (top) and cross-sectional (bottom) view of the exemplary appliance/superstructure.

FIGS. 5 and 6 depict an alternative structure for the therapy appliance. In these embodiments, the appliance comprises a flexible or semi-rigid material 501 and 603 (referred to hereinafter as a "membrane") that is attached to a skeletal superstructure 502 and 602 overlying the membrane. The skeletal structure can be made of injection molded plastic and provide "snap" or "fastening" points 601 to retain the membrane away from the skin surface when the device is in use.

Figure 7:
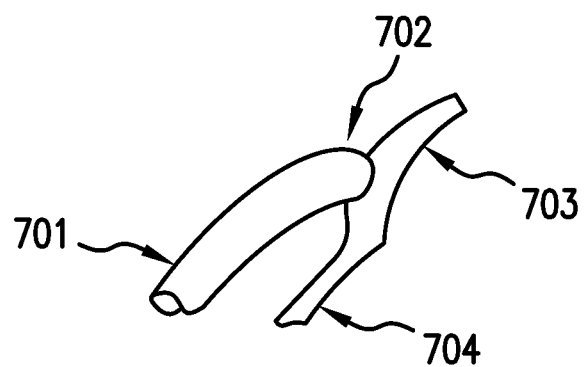
FIG. 7 depicts a detailed view of a region at which the exemplary appliance/superstructure mates to the user's skin surface.

In certain embodiments, the skeletal structure can house one or more of the additional modules of the ambulatory device. An example of such a module 503 is depicted in FIG. 5. The skeletal superstructure can provide conformal fitting to the various anatomical shapes of the users, and provide compliant support to the silicone material on the periphery on the appliance to provide sealing combined with low skin contact pressure. This superstructure can be provided in multiple standard sizes to improve the ability to conform to various anatomies. As depicted in FIG. 7, the mount points 703 at which the membrane 704 seals to the user's skin can be made to pivot at a point 702 of the skeletal structure 701 to more accurately fit anatomical contours, and the added flexibility of the soft membrane can act to distribute the seal pressure load across a large surface for added comfort.

Figure 10:
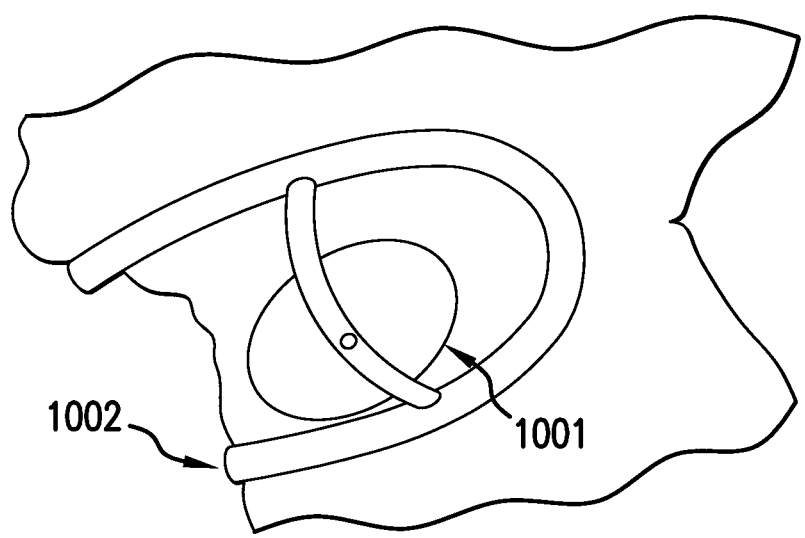
FIG. 10 depicts an alternative exemplary therapy appliance comprising an asymmetric single appliance or a bilateral pair of appliances attached to a superstructure.

In another alternative depicted in FIG. 10, the therapy appliance can be provided as a single unit 1001 to be positioned asymmetrically on the user's neck, or as a pair of units 1001 positioned bilaterally on both sides of the user's neck. These units may be supported by a rigid or semi-rigid superstructure 1002 for positioning and mating to the user.

The portions of the therapy appliance in contact with the skin may require regular cleaning, as debris may reduce the effectiveness of the seal, causing the vacuum to degrade prematurely. In the case of the superstructure embodiment, the membrane, which can be made from silicone, can be provided as a disposable component. This is particularly advantageous to sealing, in that the contact points of the appliance to the skin may tend to wear from friction, and/or to pick up debris (particularly if an adhesive, gel or other surface treatment is used to improve sealing). It is also advantageous from a hygienic point of view, as the portion of the appliance in contact with the skin can be regularly changed.

A certain amount of leakage at the seal may be tolerated so long as the desired therapeutic vacuum level can be achieved and maintained for the therapy period. Nevertheless, sealing of the device to the user's skin is important to maintain the vacuum in a useful therapeutic range without depleting battery power. An appropriate type of seal is classified a gasket or compressive seal. For low compressive values the leakage is significantly influenced by the relative roughness of the contact surfaces. Any microscopic undulations on the surface of the skin can hold the appliance surface off the surface of the skin and provide a vacuum leak path. Thorough shaving, washing to remove dead skin particulate, and applying face creams may provide an added benefit to sealing.

Figure 15:
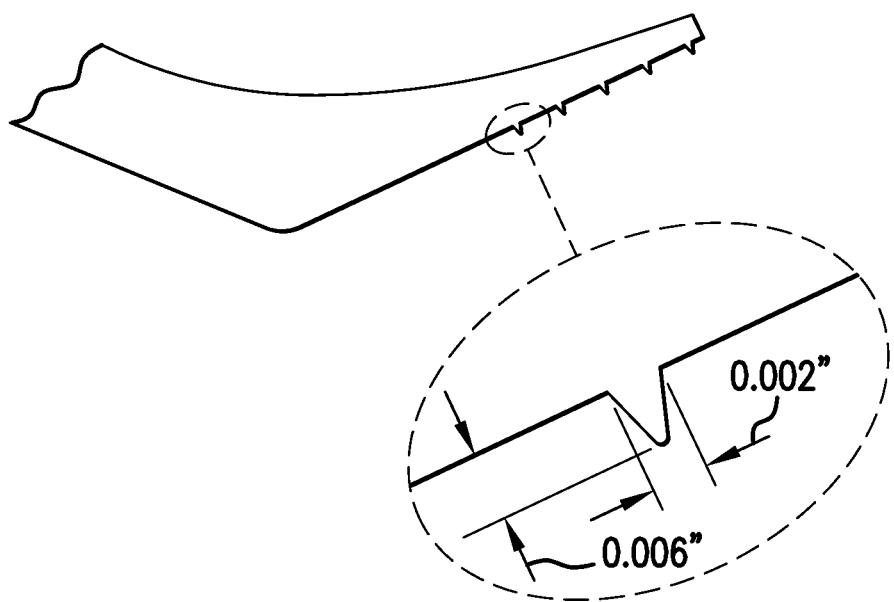
FIG. 15 depicts detailed views of a contact surface of the appliance comprising ridges to enhance sealing to the user's skin surface.

In certain embodiments, the peripheral contact surfaces of the appliance can provide a series of continuous "ridge lines" as depicted in FIG. 15 that run roughly parallel to the periphery of the seal. Suitable dimensions for these ridges would be between 0.005 and 0.05 inches tall and between 0.005 and 0.05 inches wide in their maximal dimension. These ridge lines may be roughly triangular or hemispherical in cross-section for ease of tooling production, although other shapes may also be provided. A preferred dimension of about 0.01 inches tall and 0.01 inches wide in maximal dimension. In a roughly triangular cross-section as depicted in the example in FIG. 15, this maximal dimension refers to the width of the base of the triangle.

These ridges would impart high local contact loads on the skin minimizing the bridging or tenting of the contact surface, while the ridges engage a contact area that is sufficiently small that the physiological impact to the tissue cell would be negligible. Other materials that enhance sealing are adhesives, gels and creams which fill the silicone/skin gaps with compliant material that have the ability to resist the differential air pressure forces. Medical body adhesives and sealing gels are known in the art, including various silicones and hydrogels.

In addition, or in the alternative, the peripheral contact surfaces may be made of a softer, more compliant material than the structural regions of the appliance. A reduction in durometer to between 15 and 30 (roughly the hardness of chewing gum or rubber band) can permit the contact surface to better fill the contours of the skin. Numerous semi-cured or uncured rubbers having an almost gel-like consistency are known in the art. These materials have the advantage of being injection moldable, and may be joined to the structural regions of the appliance in a 2-part molding process.

Figure 16A:
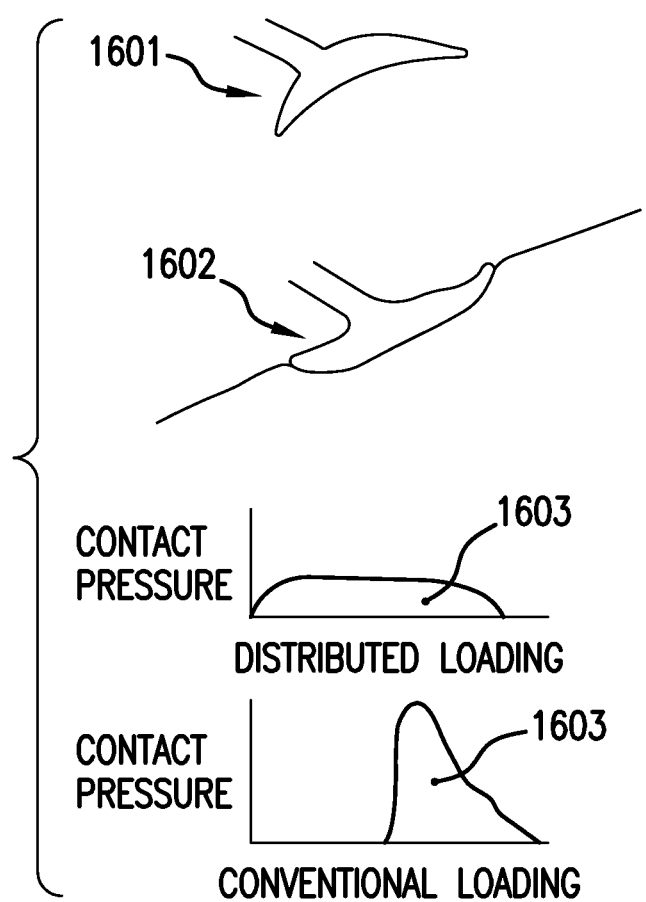
FIG. 16. Depicts detailed views of a contact surface of the appliance comprising a surface provide configured to distribute contact pressure across a greater skin surface area.

Because the contact surface of the appliance applies a force to the user's skin (which may be perceived by the user as pressure against the skin) due to the forces generated by the therapeutic vacuum, a lack of comfort may result in a failure to use the appliance. Under certain circumstances, the capillaries, arterioles, and venules in the skin underlying the edge or lip may also collapse under prolonged use. Thus, the contact surface is preferably configured to distribute the force load across a sufficient skin area to minimize the force load on localized pressure "hot spots." An example of such a distributed seal is depicted in FIG. 16A. In this example, a relatively low durometer material may be provided as a mating surface 1601 which, upon mating to the user's skin surface, deforms (1602) and seals the appliance to the user. This can act to distribute the total contact pressure (the area under curves 1603) across a greater surface area. Preferably, no pressure along the contact surface with the user's skin exceeds 60 mm Hg, preferably 40 mm Hg, more preferably 30 mm Hg, and most preferably 25 mm Hg, which approximates the mean venous pressure during sleep in humans. Alternatively, or in addition, the partial vacuum can be cycled during at least part of the therapy period to a lower level to vary the force load at the contact surface with the user's skin.

Figure 16B:
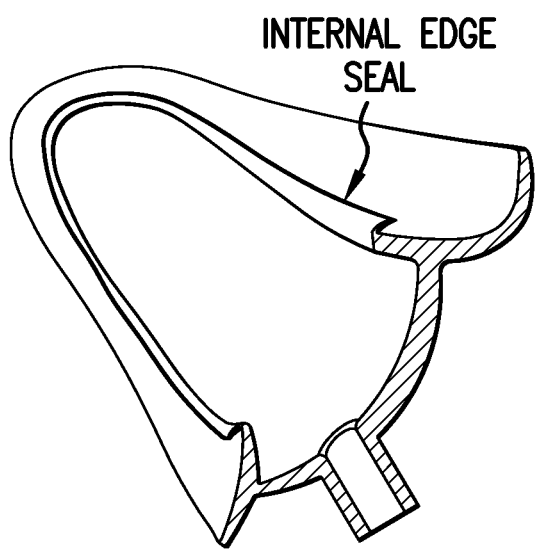
Figure 16C:
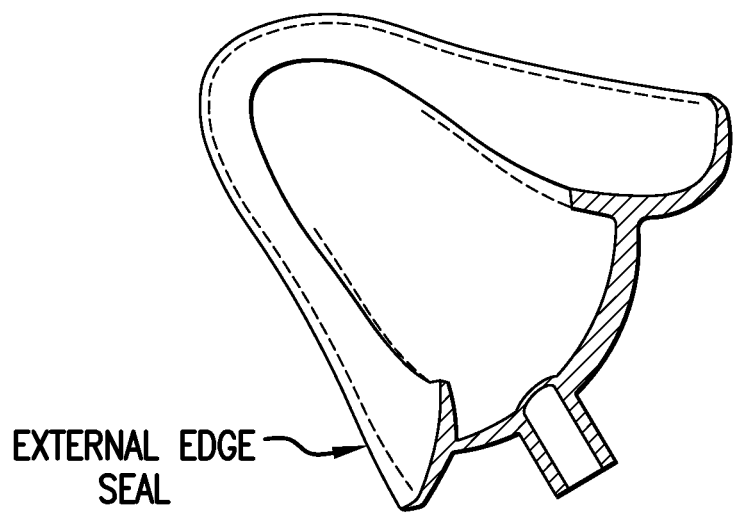

FIG. 16B depicts an alternative form for such a distributed seal. In this figure, a flap projects from the leading edge outward from the vacuum chamber and under the sealing edge. FIG. 16C depicts another alternative for such a distributed seal. In this figure, a flap projects outward from the sealing edge. In each case, this flap provides a seal area where the appliance seats against the skin. In the case of FIG. 16B, the entire area under the sealing edge is not subjected to the vacuum, so the total area subjected to vacuum is less and therefore the skin contact pressure is reduced. In certain embodiments, this flap area is made of a thin silicone rubber, and is orientated outward or against the differential pressure. In this way, the differential air pressure loads on the seal tend to tighten the seal rather than cause it to lift off. The thickness of the flap is preferably in the range of 0.002 to 0.010 inches. The material may be provided with thicker regions (e.g., a thickness of about 0.040 inches at the shank) to prevent the material from rolling up on itself.

B. Creating a Partial Vacuum—the Air Pump

The term "air pump" as used herein refers to a device that removes gas molecules from a sealed chamber in order to leave behind a partial vacuum.

Figure 13:
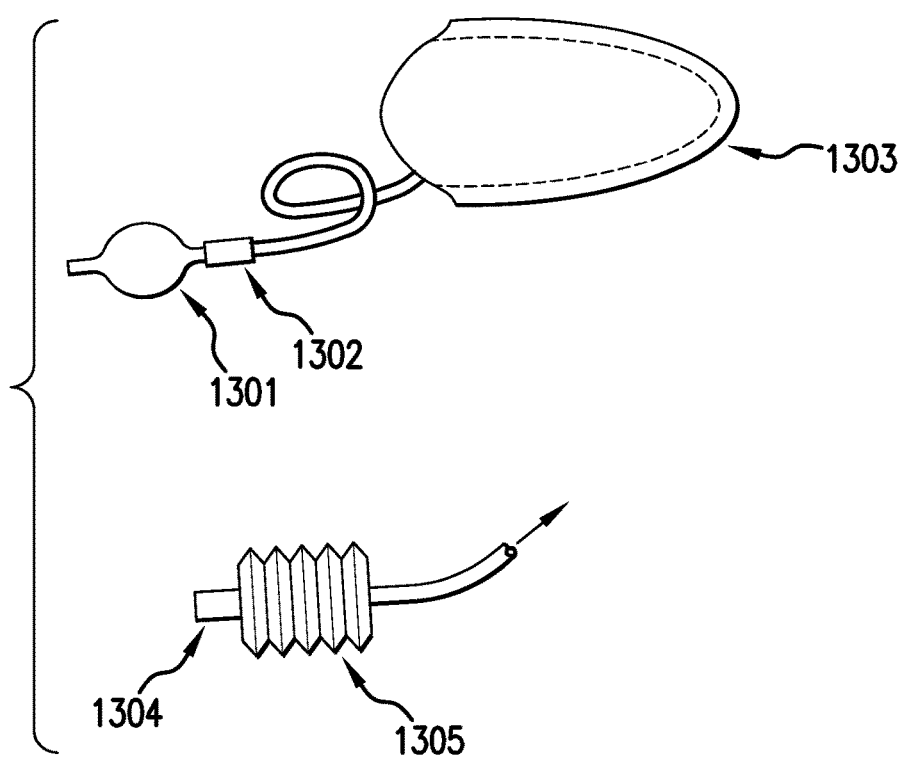
FIG. 13 depicts exemplary therapy appliances that rely on manual, rather than electrically-driven, pumps for generation of a partial vacuum.
Figure 14:
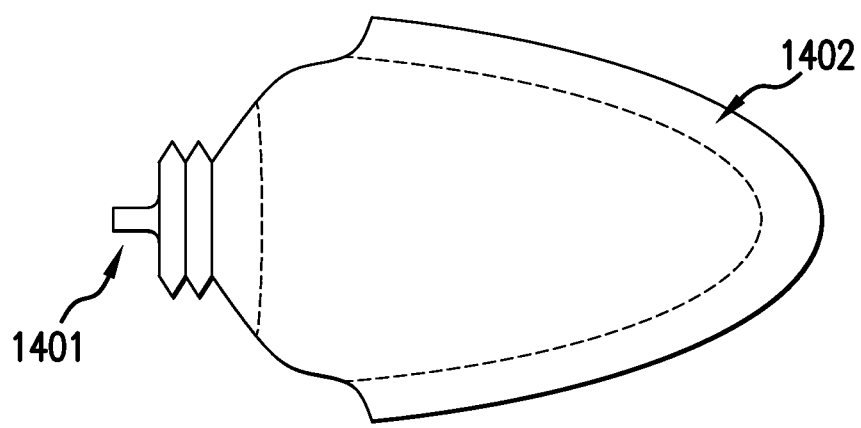
FIG. 14 depicts an alternative configuration of a therapy appliance that relies on a manual pump for generation of a partial vacuum.

A vacuum may be created within the chamber formed by the appliance and the user's skin surface in a number of ways. A simple method is to manufacture the therapy appliance using a resilient memory-shaped material that may be compressed like a bulb, mated to the user's throat, and then released. In this case, when the appliance is mated to the throat and the appliance released, return of the appliance to its original shape creates a partial vacuum within the space. As another example, a pleated section 1401 of the appliance as depicted in FIG. 14 may be used to provide a hand-driven air pump. Another manual method is to provide a hand pump such as 1301 and 1305 separate the therapy appliance as depicted in FIG. 13. When the appliance is mated to the user's throat, the hand pump may be used to evacuate air from the chamber through check valve 1302 or 1304.

A preferred powered design for a pump module utilizes a positive displacement pump, most preferably a diaphragm pump driven by either a linear motor, or a brushed or brushless DC rotational motor drive. In particularly preferred examples in which a linear motor is used, the linear motor is operatively linked to control circuitry configured to drive single discrete strokes of the pump as well as multiple strokes. In particularly preferred examples in which a DC motor is used, the motor is operatively linked to a controller configured to drive single discrete revolutions of the motor as well as multiple rotations. Examples of these and other suitable air pumps are described below.

a. Air Pump Types

The term "positive displacement pump" as used herein refers to a mechanism to repeatedly expand a cavity, allow gas molecules to flow into the cavity from the chamber, seal off the cavity, and exhaust the gas molecules to the atmosphere. Of the "positive displacement" type of vacuum pumps there are preferred candidates: vane pumps and diaphragm pumps.

Vane pumps move gas through the pump using a rotating assembly in the pumping chamber that move the gas from inlet to outlet. As the rotor turns, the ends of the vane barely touch the housing, creating a seal from inlet to outlet. The gas is pressurized as the volume between the vanes lessens during one half-cycle and is suctioned through an intake port during the other half-cycle. Vane pumps create pressure pulses equal to the number of vanes contained within the pump and the speed at which the vanes are turned. The vane type pump does not maintain a vacuum throughout the pump circuit, and therefore the system would include a check valve between the pump and the enclosed partial vacuum chamber to prevent vacuum loss. Such pumps have very low starting torque and would be well suited for use with a DC motor. In comparison with other pumps, the noise frequency created will be higher and therefore may work well with sound abatement technologies described below.

Diaphragm pumps are popular for small to medium size applications as an alternative to vane pumps. Diaphragm pumps can be extremely low maintenance and quiet. Diaphragm pump function by mechanically moving a diaphragm which displaces air. A pair of one way valves is provided to direct the movement of air, thereby creating the vacuum. These valves will also provide the necessary function of sealing the pump circuit from the enclosed partial vacuum chamber.

Within this pump category there are several ways in which diaphragm movement is achieved. Linear pumps can connect the diaphragm directly to an armature and vibrate the armature in a linear direction. Motor control in this type of pump can be very simple. A linear motor driving a linear pump can move a diaphragm very slowly, which may be advantageous from the point of view of noise and vibration creation. Rotary diaphragm pumps stroke the diaphragm with a rotary to axial mechanical converter. They have low starting torque and can be coupled with DC motors. These pumps are inexpensive.

In another alternative, an air pump may be a dynamic pump such as a regenerative pump. In a regenerative pump, an impeller rotates, creating a centrifugal force which moves the air molecules from the blade root to its tip. Leaving the blade tip, the air flows around the housing contour and back down to the root of a succeeding blade, where the flow pattern is repeated. This action provides a quasi-staging effect to increase pressure differential capability. The speed of the rotating impeller determines the degree of pressure change. Such pumps are best used for external (e.g., tabletop) vacuum sources, as opposed to a vacuum source supported on the user as described herein.

A particularly preferred pump is a diaphragm pump having a single stroke displacement of between 0.001 and 0.01 $in^3$, and most preferably in the range of 0.003 to 0.005 $in^3$. A pump with a displacement of about 0.004 $in^3$ will yield a maximal evacuation rate of 12 $in^3$/min when driven at 3000 rpm using a rotary brushless DC motor or 60 Hz using a linear DC motor. This could completely evacuate an appliance enclosing a volume of between 0.5 and 2 in$^3$ in 2.5 to 60 seconds. Of course, complete evacuation of the chamber enclosed by the appliance is not required to generate a therapeutic level of vacuum. For example, in an appliance providing an 8 in$^3$ chamber, removal of about 1.6 in$^3$ can provide an appropriate working pressure. Thus, a full pumping mode of 1 to 25 in$^3$/min can quickly generate therapeutic vacuum levels within the appliance.

Following the initial evacuation, the air pump is driven only as needed to maintain the partial vacuum above the desired threshold. Assuming a leakage rate of air into the enclosed chamber at a rate of between 0.005 and 0.5 in$^3$/min, the diaphragm pump could be driven to pulse a single stroke only once every few seconds to few minutes. This dual evacuation/quiet mode approach has numerous advantages, including being extremely quiet and low in both vibration and battery consumption. For example, a preferred pump can run in quiet mode at a rate of between 0.005 and 0.5 in$^3$/min (most preferably at 0.01 and 0.1 in$^3$/min), which can remove between 2.4 and 240 in$^3$ of air in an 8 hour night. Given a pumping rate of 5 strokes a second and a pump displacement of 0.004 in$^3$/stroke, such a pump could run 0.25 to 25 seconds out of each minute and still deliver the desired performance.

b. Electric Motor Types

This application requires both slow and fast operation, low sound production, and efficient battery usage. In a DC motor, when the motor is provided with its rated voltage, the motor operates at full rpm. To control speed, one must turn the motor off for a short period of time. This motor voltage is provided typically as a square wave. The frequency of this square wave is typically very fast (optimally in a range of from 2,000 to 18,000 Hz), and the amount of power the motor receives is proportional to the percentage of time the square wave is "on" versus "off." This technique is called pulse width modulation (PWM). PWM accommodates the slow motor speed operation required of the "quiet mode" as short pulses of full voltage create strong magnetic fields that force highly controlled partial rotations. Running in the very slow speed range may require the addition of an encoder to provide feedback to a controller for accurate speed control.

C. Vacuum Control

Vacuum control may be provided by both mechanical and/or electronic control mechanisms. A simple mechanical mechanism to control the vacuum within the appliance chamber is to provide a miniature vacuum relief valve press fit into a port in the appliance. The relief valve is selected to admit air when a preselected vacuum level is exceeded. The air pump is then driven at a constant speed, with the vacuum release valve controlling the partial vacuum by opening when the vacuum exceeds a desired level and closing below that level. Preferred operational vacuum levels are selected within a range of between about 7.6 cm to about 61 cm of water by inserting an appropriate vacuum relief valve. No monitoring of internal vacuum or control of the motor driving the air pump is necessary in this embodiment. However, this embodiment would tend to provide unnecessary noise and to use battery power at a potentially undesirable rate.

Figure 3:
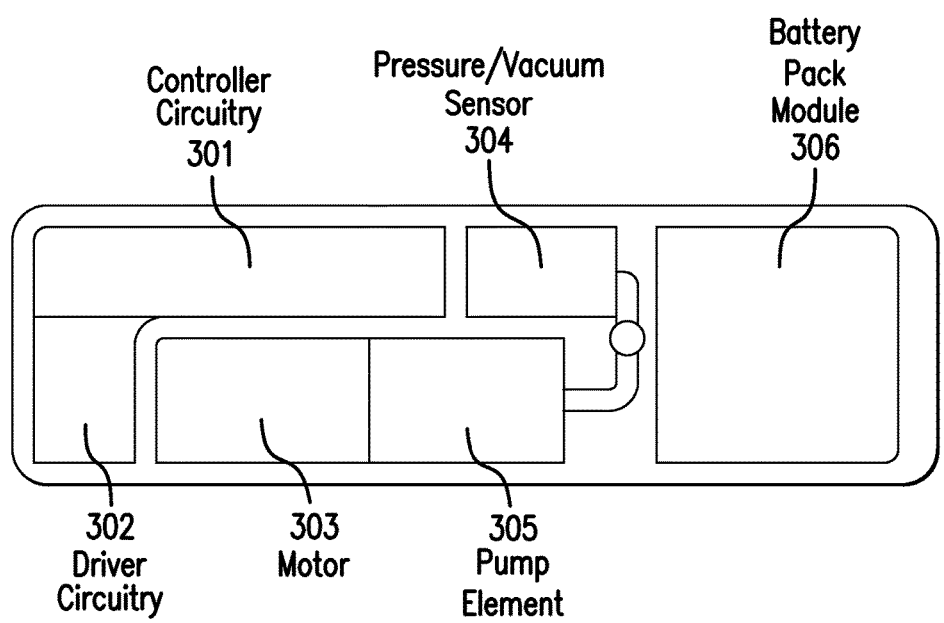
FIG. 3 depicts an exemplary schematic layout of elements contained within the electronics and mechanical module.

A preferred electronic/mechanical vacuum control mechanism may comprise a microcontroller coupled to a vacuum or pressure sensor and motor control circuitry. FIG. 3 depicts, in block form, an exemplary mechanical/electronic module. This preferred embodiment includes a vacuum pump module comprising a motor 303 and pump element 305, a battery pack module 306, and control module comprising a pressure/vacuum sensor 304, controller circuitry 301, and driver circuitry 302, all within in a single housing. In an exemplary embodiment, the housing is approximately 0.75×1.75×3.00 inches in size.

Figure 4:
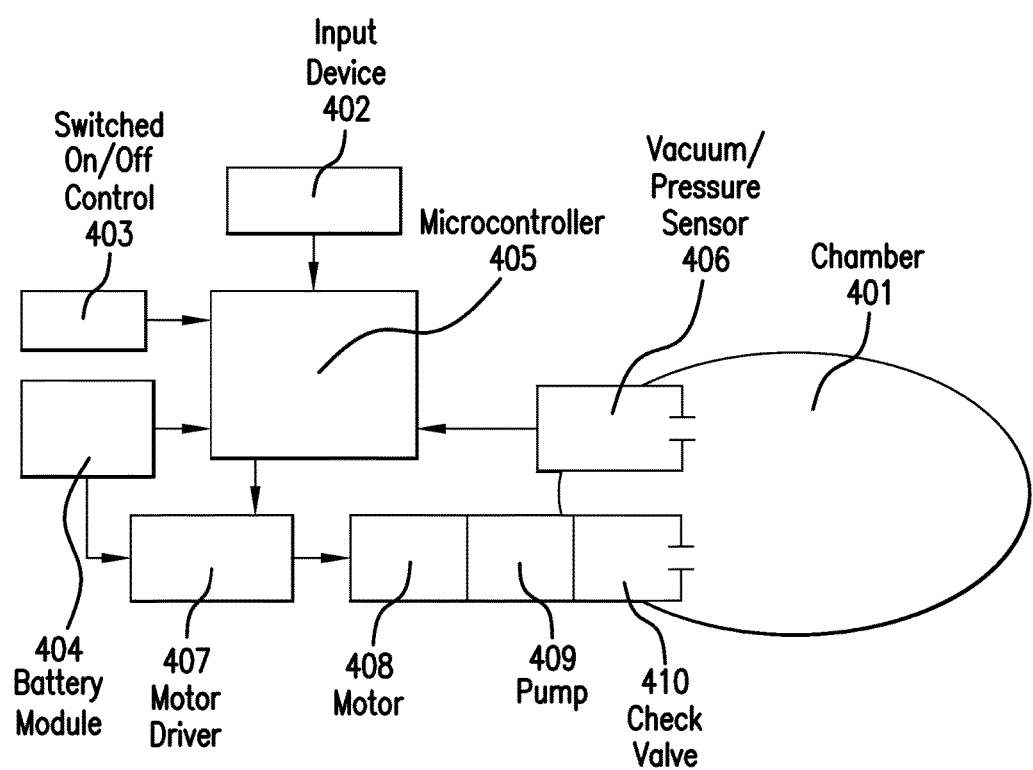
FIG. 4 depicts an exemplary layout of elements contained within the electronics and mechanical module in block diagram form.
Figure 19:
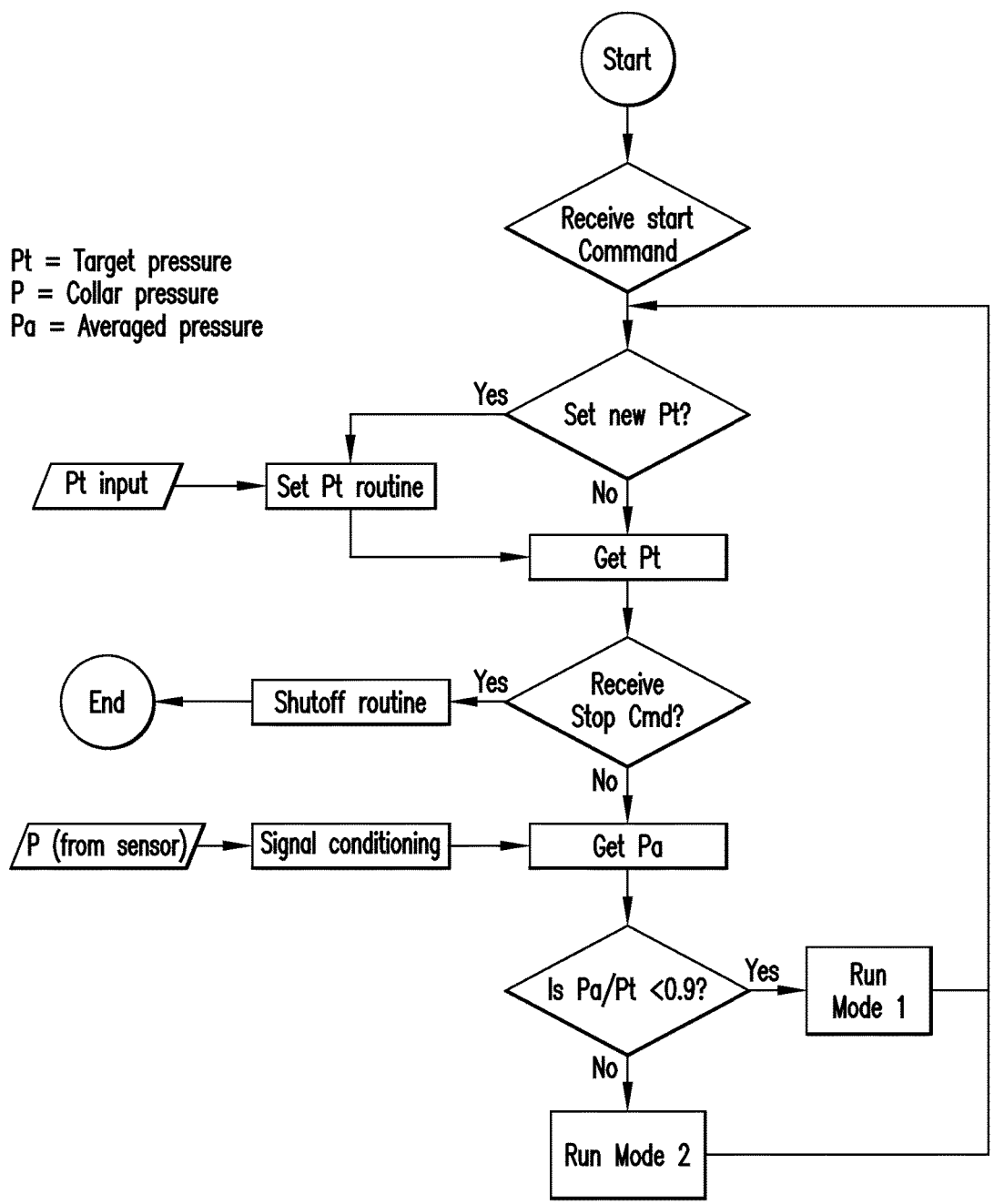
FIG. 19 depicts an exemplary vacuum control flow diagram.

A typical control module is depicted in FIG. 4. This contains, inter alia, a battery module 404 providing power for the systems, a switched on/off control 403 for the vacuum and electronics systems, and the control electronics for instructing the vacuum system in order to maintain a therapeutically effective vacuum. An input device 402 is provided to enter the desired partial vacuum level to the microcontroller 405. Suitable microcontrollers 405 include the Atmel ATmega48, ATmega88, or ATmega 168. Each is an 8-bit microcontroller containing an arithmetic logic unit, flash memory, and I/O functions. In the case of a brushless DC motor, a quadruple half-H driver such as the Texas Instruments L293 is appropriate. In its most compact form, the electronic control circuit may be integrated on the same circuit board as the motor driver 407. To maintain vacuum stability within the chamber 401, the microcontroller compares current versus target vacuum by using a vacuum/pressure sensor 406 and a PID (proportional, integral and differential) loop. The controller will then direct the pump 409/motor 408 accordingly. An exemplary control flow chart for this purpose is provided in FIG. 19. A check valve 410 can be provided to permit removal of air from the chamber, while preventing leakage into the chamber 401 from the pump.

Numerous optional components can be employed to improve the performance and control of the device. For example, because the volume enclosed by the appliance and the user's skin is approximately known, the time to achieve the partial vacuum can be calculated. The vacuum or pressure sensor detects a drop in vacuum that requires energizing the pump and motor. If it is determined that the partial vacuum has not been achieved in some appropriate time, the vacuum source can be deactivated, and optionally an alarm condition indicated. Suitable alarms can include visual (e.g., a light), auditory (e.g., a tone), and/or tactile (e.g., vibration) indicators.

Additionally, as discussed above, the partial vacuum can be cycled during at least part of the therapy period to a lower level to vary the force load at the contact surface with the user's skin. This cycling can advantageously be synchronized to coincide with the inspiration/expiration cycle such that the partial vacuum is increased during inspiration. This requires that the control circuitry communicate with sensors for detecting inspiration/expiration, and that the chamber formed by the appliance permit rapid changes in the partial vacuum. This is similar to the continuous positive airway pressure (CPAP) therapy of a type known as "bi-level CPAP," which synchronizes airway pressure levels with the inspiratory and expiratory phases of respiration.

Figure 18:
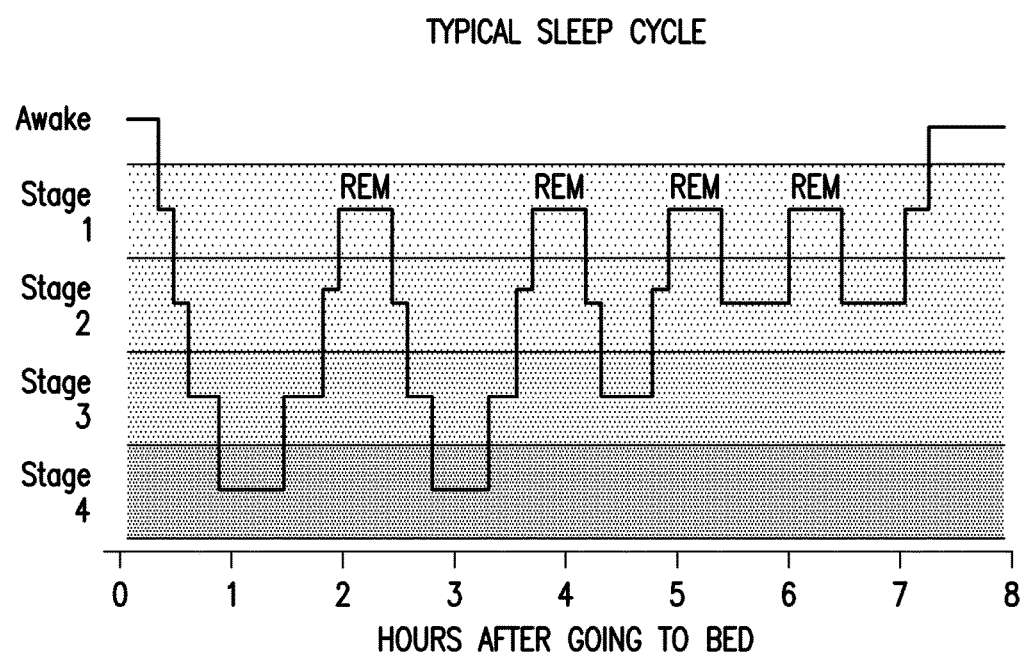
FIG. 18 depicts a typical human sleep cycle.

In another embodiment, the vacuum may be adjusted to coincide in some way with the sleep cycle of the user in order to improve comfort and reduce arousal during sleep. A typical sleep cycle is depicted in FIG. 18. One possibility is to create greater partial vacuum levels during sleep stages 3 or higher, and reduced vacuum levels at stages 1 or 2 when the user may be more easily aroused. Alternatively, greater partial vacuum levels may be created up to about 5 hours of sleep, beyond which the user will be in a generally more arousable state. In another alternative, lower partial vacuum levels may be provided during the first and last two hours of sleep, when noise generally has the greatest disruptive effect on the sleep cycle.

The vacuum can also be controlled to achieve increased vacuum levels during or immediately after an event, such as the onset of snoring or apnea. Such lower usage levels of the mechanical elements of the ambulatory device can minimize sound and vibration levels produced by the appliance, and may provide additional comfort to the user in those periods where the airway is not obstructed. Apnea events may be detected from cardiac interbeat interval time measurements, respiration measurements, pulse oximetry, etc., and snoring events may be measured acoustically, by vibration measurement, etc. Numerous sensor types, such as thermistors used to measure respiration airflow temperature, acoustic sensors used to measure breath sounds and snoring, oximeters used to measure oxygen levels in the blood, vibration sensors used to breathing-induced vibrations, etc. are known in the art for sensing respiratory cycles, apnea events, and snoring events.

The controller can also be programmed to filter the information received from such sensors in order to enhance system control and adapt the vacuum system to changing patient conditions. For example, the controller can be programmed to recognize sensor data indicating that a body movement, such as a swallowing or coughing event, has momentarily increased the vacuum within the chamber, and pause the air pumping system until the vacuum returns to a more normal level. The controller can also recognize sensor data (such as from accelerometers, attitude sensors, etc.) indicating body position (on side versus on back versus upright for example).

In another example, the controller can be programmed to recognize sensor data indicating an apnea or snoring event. The vacuum may be increased from a preset therapeutic level during the event until sensor data indicates the event has terminated. After the event, the vacuum may be returned to the pre-event level. Alternatively, the vacuum may be held at the higher level, and the therapeutic vacuum level stored in the controller may be set to this new, higher, level such that future use of the appliance will begin from this new preset therapeutic level. In yet another example, the controller may be programmed with a number of apnea or snoring events per night considered tolerable, and the controller may count events or length of events, and if they exceed some threshold number, adjust the vacuum upward until the events are reduced by 20% or more in number or duration. In this way, the system may self-adjust, based on feedback received from the sensor(s).

The controller may also keep track of a variety of measures for later reporting to a caregiver. Examples include an "apnea index" (defined as the number of apneic episodes/hour use of the appliance); a "snoring index" (defined as the number of snoring episodes/hour use); an "apnea-hypopnea index" (defined as the total apneas plus hypopneas/hour use); and/or a "respiratory distress index" (defined as the total apneas, hypopneas, and other respiratory disturbances such as snoring arousals, hypoventilation episodes, desaturation events, etc./hour use).

Optionally, the controller circuitry is programmable, allowing the user or medical personnel to alter various parameters, such as vacuum levels, alarms, sensor types, etc., as well certain optional features such as noise compensation.

a. Vacuum/Pressure Sensor(s)

As discussed above, a vacuum sensor to determine the differential between the chamber partial vacuum and ambient atmospheric pressure may be connected to the controller, and is used to maintain the partial vacuum at a desired level. Suitable micromachined silicon sensors in pc board-mountable packages are known in the art. These sensors may include temperature compensation or calibration circuitry, or such circuitry may be optionally provided as separate electronic components. A vacuum pressure transducer typically provides a voltage output that is proportional to changing pressure (e.g., increasing vacuum), while an absolute pressure transducer typically provides a voltage output proportional to increasing pressure (e.g., decreasing vacuum).

D. Data Import and Export

The microcontroller is preferably operably connected to a data input device such as a keypad or touchscreen to allow the user or medical personel to, among other things, set the desired level of partial vacuum. In CPAP, the positive pressure applied during long-term treatment is generally determined by a technician in the sleep laboratory on the basis of a continuous polysomnographic recording. The treatment pressure is increased until apneas, hypopneas and snoring are adequately reduced during all sleep stages and in the supine position. This fixed pressure is then used for home therapy. Likewise, the level of partial vacuum necessary to prevent apneas, hypopneas and snoring may be determined in a sleep laboratory, and this level of vacuum set into the control module. In simple form, a single button may be repeatedly depressed, with the number of button presses counted and converted to a vacuum setting by the microcontroller. In more complicated devices, a display might provide a digital readout of the current setting, and up/down arrow keys used to increase/decrease the setting. Finally, a keypad may be employed to simply type in a desired setting. In all cases, the data input device may communicate with the control module in a wired or wireless manner. In the case where the caregiver is setting the vacuum level, it may be advantageous to have the data input device be either separate or removable from the control module so that alterations cannot be made in an uncontrolled manner.

Among other things, sleep apnea can increase arterial pressure and heart rate and reduce blood oxygen content. It has been reported that suffering from obstructive sleep apnea increases an individual's risk of having a heart attack or dying by 30% over a period of four to five years. Thus, medical monitoring of apnea treatment success can potentially provide life-saving benefits. In certain embodiments therefore, the devices described herein monitor and store and/or transmit vital signs and user characteristics measured during use of the therapeutic appliance.

The apparatuses of the present invention may be configured to record and/or respond to various characteristic sensors. The term "characteristic sensor" as used herein refers to a sensor which detects some characteristic of the user and generates an electronic result corresponding to that characteristic. As noted above, numerous sensor types, such as thermistors, acoustic sensors, oximiters, vibration sensors, etc. are known in the art for sensing respiratory cycles, apnea events, and snoring events. U.S. Patent Publication 2006/0009697, which is hereby incorporated by reference in its entirety, discloses a single, low-profile, disposable system that measures a variety of vital signs, including blood pressure, without using a cuff. This and other information can be easily transferred from a patient to a central monitor through a wired or wireless connection. For example, with the system a medical professional can continuously monitor a patient's blood pressure and other vital signs during their day-to-day activities, or while the patient is admitted to a hospital. This system can also characterize the patient's heart rate and blood oxygen saturation using the same optical system for the blood-pressure measurement. This information can be wirelessly transmitted along with blood-pressure information and used to further diagnose the patient's cardiac condition.

Such sensors may be worn by the user during use of the therapy appliances described herein. The resulting information has many uses for patients, medical professional, insurance companies, pharmaceutical agencies conducting clinical trials, and organizations for home-health monitoring.

Data import and export may be by wired and/or wireless means. The term "wired" in this context refers to any method in which there is a physical contact which operably connects the control module to an external device, such as a PDA, computer, cellular telephone, network connection, etc., which sends data to or retrieves data from the control module. The term "wireless" refers to any method in which data is sent to or retrieved from the control module without a physical connection.

In the case of a wired data transfer, a cabled USB connection between the control module and the external device is one example that may be provided. While USB type connections have become ubiquitous, any form of connection where contacts on one device physically meet contacts on another device. Alternatively, a memory card, such as a Memory Stick, Secure Digital, Flash memory drive, etc., may be used to transfer data by moving the memory card between the control module and the external device.

In the case of a wireless data transfer, numerous standards well known in the art may be used. Such wireless connections include various radio frequency and optical (e.g., infrared) connections that are known in the art. For relatively short distance RF communications, Bluetooth, HomeRF, IEEE 802.11b, IEEE 802.11a, and IEEE 802.15.4 are well known standard communications protocols that may be used. For somewhat longer range data transfers, cellular telephone protocols such as CDMA, TDMA, GSM, and WAP may be employed.

These methods need not be used in isolation, but instead may be advantageously employed in combination. For example, the control module may communicate at a short distance with a local "base station" by a wired or wireless mechanism, and the base station may then communicate with an external device, for example at a caregiver's office or central data collection point, using one of the cellular telephone protocols, or through telephone twisted pair, cable TV, or other wiring existing in the user's location. This can extend battery life in the control module by lowering power requirements for communication, while the base station may be powered by line voltage.

E. The Ambulatory "Integrated" Appliance

A preferred ambulatory therapy appliance of the present invention has the following minimum characteristics: (i) the therapy appliance is a biocompatible single integral element that carries the vacuum load and provides a seal at the skin interface having a low leakage rate of air into the enclosed chamber, and preferably a rate of between 0.005 and 0.5 in$^3$/min (most preferably at 0.01 and 0.1 in$^3$/min); (ii) the therapy appliance wearably supports a battery powered air pump that maintains a working vacuum at a sound level of less than or equal to 40 dB SPL, more preferably less than or equal to 35 dB SPL, still more preferably less than or equal to 30 dB SPL, and most preferably less than or equal to 25 dB SPL.

By way of comparison, a typical living room, or quiet office has a sound level of about 40 dB SPL, a library or soft whisper at 5 Meters has a sound level of about 30 dB SPL, and a broadcasting studio has a sound level of about 20 dB SPL. The term "maintains a working vacuum" refers to maintenance of an already achieved vacuum level above a desired threshold against leakage of air into the therapy appliance. The initial vacuum may be achieved while the user is awake, when noise is less of an issue, and then maintained in quiet mode while the user sleeps.

In preferred embodiments, the air pump is provided as a diaphragm pump having a single stroke displacement of between 0.001 and 0.01 in$^3$, and most preferably in the range of 0.003 to 0.005 in$^3$, driven using a rotary (brushed or brushless) DC motor or a linear DC motor.

The ambulatory therapy appliance optionally includes one or more of the following elements:

(i) A peripheral seal that distributes force loads across a sufficient skin area to minimize peak localized contact pressures. Preferably, no pressure along the contact surface with the user's skin exceeds 50 mm Hg, preferably 40 mm Hg, more preferably 30 mm Hg, and most preferably 25 mm Hg;

(ii) The air pump is operably connected to vacuum control module comprising a microcontroller coupled to a vacuum or pressure sensor, and motor control circuitry which controls the pump on/off cycles and/or speed. Most preferably, the vacuum control module is programmed to control the pump to maintain the working vacuum by operating the air pump discontinuously. The therapy appliance preferably wearably supports this control module;

(iii) The control module is operably connected to a data input device such as a keypad or touchscreen; and/or is provided with a wired and/or wireless connection to an external device for data transfers;

(iv) The air pump, driving motor, battery, and control module are provided in a single housing, which is preferably wearably supported by the therapy appliance;

(v) The vacuum control module is programmed to cycle the partial vacuum to a lower level during at least part of the therapy period. This cycling can advantageously be synchronized to coincide with the inspiration/expiration cycle such that the partial vacuum is increased during inspiration;

(vi) The therapy appliance comprises a buffering component configured to dampen swings in the partial vacuum created within the appliance by user movement. In certain embodiments, a housing comprising one or more of the pump, driving motor, battery, and control module overly the buffering component so as to protect it from physical contact with foreign objects during use;

(vii) The battery is inductively charged;

(viii) The therapy appliance is used together with sound masking and/or sound cancellation electronics to at least partially mask the noise created by the mechanical and electronic components. These electronics may be used by the user of the therapy apparatus, and/or by the spouse or companion of the user. In certain embodiments, the sound masking and/or sound cancellation electronics are wearably supported by the therapy appliance, however, they may also be provided separately;

(ix) The therapy appliance comprises one or more characteristic sensors, the results of which are used by the controller for control of the apparatus and/or are stored for later access, display, or data transmission from the storage location to an external device;

(x) The therapy appliance comprises a strap to maintain position on the user during periods of low vacuum, such as when the partial vacuum is cycled to a lower level during at least part of the therapy period.

a. Battery Modules

Numerous battery technologies are known in the art, including common alkaline batteries, oxyride batteries, lithium batteries, etc. There are three preferred battery technologies that could be employed: Nickel Cadmium (NiCad), Nickel Metal Hydride (NiMH) and Lithium Ion (Li-ion), and most preferred are Li-ion batteries.

An exemplary power consumption for a battery-powered system will be 45 mA per hour at 4.8 volts. In such a configuration, which can be provided by a 4 cell AAA size NiMH battery pack, the systems described herein could easily operate for an 8-hour sleep period. Alternatively, a 2 cell 300 mAh Li-ion battery pack operating at 7.4 volts can provide similar performance. A most preferred system would operate for an 8-hour period using a single 3.7 volt Li-ion cell providing at least 600 mAh.

b. Recharging

Figure 8:
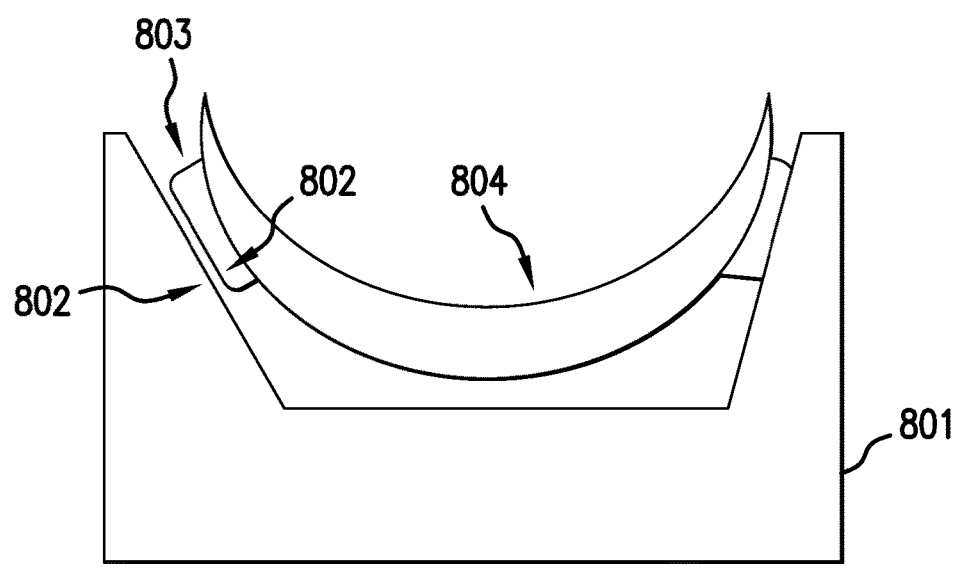
FIG. 8 depicts an exemplary therapy appliance carrying an electronics and mechanical module docked in a charging stand for inductive charging of batteries.

In the case of rechargeable batteries, the battery could be provided with a wired plug in to a conventional charger, with contacts which mate with contacts on a battery charging "station," or with an inductive coupling using an inductive coil that would be located on the surface of the vacuum module. The inductive circuit would be complete upon placing the appliance 804 or the battery-containing module 803 in a cradle or dock 801 that has a mating inductive coil 802 as depicted in FIG. 8.

F. Compensating for Movement-Induced Changes Vacuum

Prior to the present invention, it was not recognized that simple body movements can substantially change the force applied to the user's neck, due to movement-induced changes in the internal volume of the appliance. For example, if one considers an appliance having an internal chamber volume of 8.6 cubic inches affixed to an adult male, the act of swallowing can increase the volume of the chamber by some 1.7 cubic inches due to displacement of the throat, a nearly 20% increase.

Although the therapy appliance may have some ability to flex, the appliance must be sufficiently rigid to maintain a spacing between the appliance and the throat. As a result, the movement-induced increase in volume is felt as a sudden increase in the pressure applied to the throat of the user. The air pressure within the therapy appliance may be modeled using the ideal gas law, which provides that the pressure of a gas is related to the volume occupied by that air. The state of an amount of gas is determined by its pressure, volume, and temperature according to the equation $PV=nRT$, where P is the absolute pressure, V is the volume of the vessel, n is the number of moles of gas, R is the universal gas constant, and T is the absolute temperature.

If one assumes that a partial vacuum greater than about 7.6 cm H2O is required to establish a beneficial therapeutic effect, and that movement can suddenly increase the volume enclosed by the therapy appliance by 20% or more due to displacement of the throat, one skilled in the art will recognize that the increase in enclosed volume causes an equivalent 20% increase in the partial vacuum within the therapy appliance. The resulting sudden increase in the forces exerted on the tissues of the throat at the contact surfaces of the appliance can cause discomfort to the wearer, arousal from sleep, etc.

This movement-induced increase in vacuum can be particularly problematic in the case of an integrated ambulatory appliance design, as the vacuum source and associated connections to the vacuum chamber are minimized in volume. As a result, the movement-induced volume changes are more pronounced in percentage terms in comparison to the total vacuum space volume. Said another way, the smaller the volume of the appliance's internal chamber and associated vacuum system, the greater the added force caused by swallowing or coughing.

Thus, the present invention provides a buffering component to dampen these movement-induced swings in the partial vacuum created within the appliance. This may be modeled most simply as a moveable diaphragm attached to a spring. The spring tension is configured to hold the diaphragm in place when the partial vacuum is within a designed tolerance. That is, if the appliance is designed to produce a partial vacuum of about 18 cm $H_2O$, the spring would not compress or expand at this pressure. The buffer spring may be preloaded at the therapeutic vacuum level by a predetermined amount so that the diaphragm of the appliance is maintained in a predetermined position at that vacuum level. If the desired vacuum level is exceeded, as in the case of the user swallowing, the spring would allow the diaphragm to move to compensate at least in part for the sudden increase in enclosed volume. If the spring is mounted inside the diaphragm (relative to the partial vacuum), the spring would compress; if the spring is mounted outside the diaphragm, the spring would expand. Once the movement had ended, the spring would return to its original shape, thereby returning the diaphragm to its original position. The result is to buffer the increase in pressure felt by the user.

Figure 11:
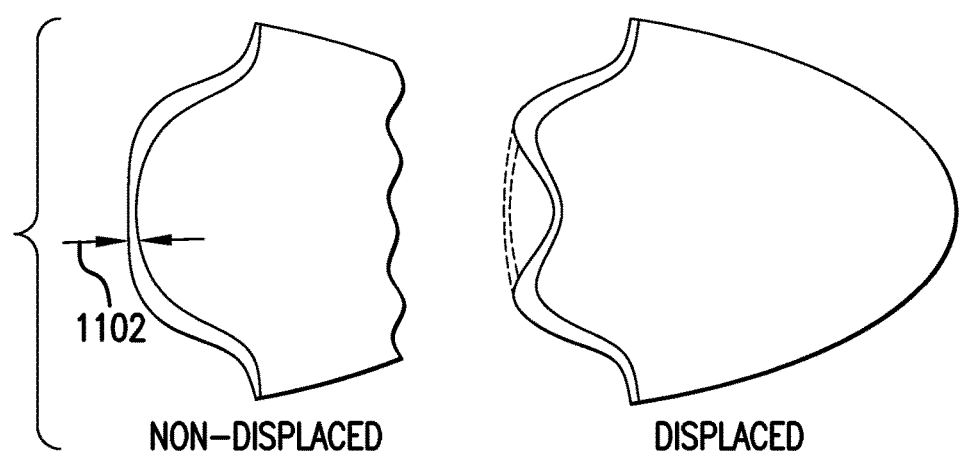
FIG. 11 depicts one example of a buffering component provided as an integral part of the therapy appliance.

Although described in terms of a spring and diaphragm, other configurations will be readily apparent to those of skill in the art. For example, a buffering component can be provided as a portion of the appliance surface which can flex inward when the internal vacuum exceeds a desired level, and then return to its original position when the vacuum increase subsides. An example of this configuration is depicted in FIG. 11, which depicts the buffering component as a central buffering region surrounded by the more rigid structural regions of the appliance. This relatively more flexible buffering region 1102 of the appliance is molded to have a tapering wall thickness from a thinner center towards a thicker, relatively less flexible outer edge. In the case of durometer 50 material, the structural regions of the appliance may have a thickness of about 0.17-0.15 in, while the buffering region may taper to a center thickness of 0.10-0.14 in. As the pressure exceeds the designed rigidity of a particular point on this region, the buffering component will begin to displace inward as depicted in FIG. 11, while thicker areas will retain their structure, as the bending point stiffness increases. As the force exerted on the region by body movement increases, it is spread across a larger surface area, increasing the ability of the region to withstand those forces. This will assist in returning the region to its original non-displaced shape once the movement-induced increase in vacuum subsides.

Figure 17:
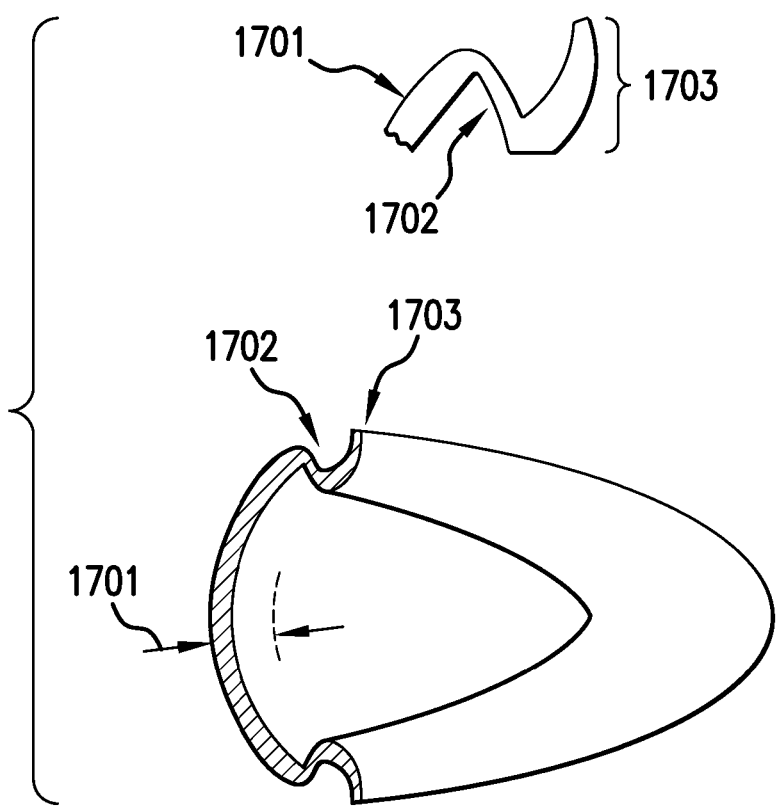
FIG. 17 depicts detailed views of an alternative buffering component provided as a flexible peripheral region of the therapy appliance.

This configuration can be essentially reversed by providing the buffering region as a peripheral region of relatively increased flexibility which surrounds the more rigid central structural regions of the appliance, as depicted in FIG. 17. In this embodiment, the outermost region 1703 of the appliance forms the contact surface with the user's skin. A flexible region 1702 lies between the contact region 1703 and the structural region 1701 of the appliance. This flexible region 1702 permits reciprocating movement of the structural region 1701 in response to movement-induced vacuum changes.

Figure 12:
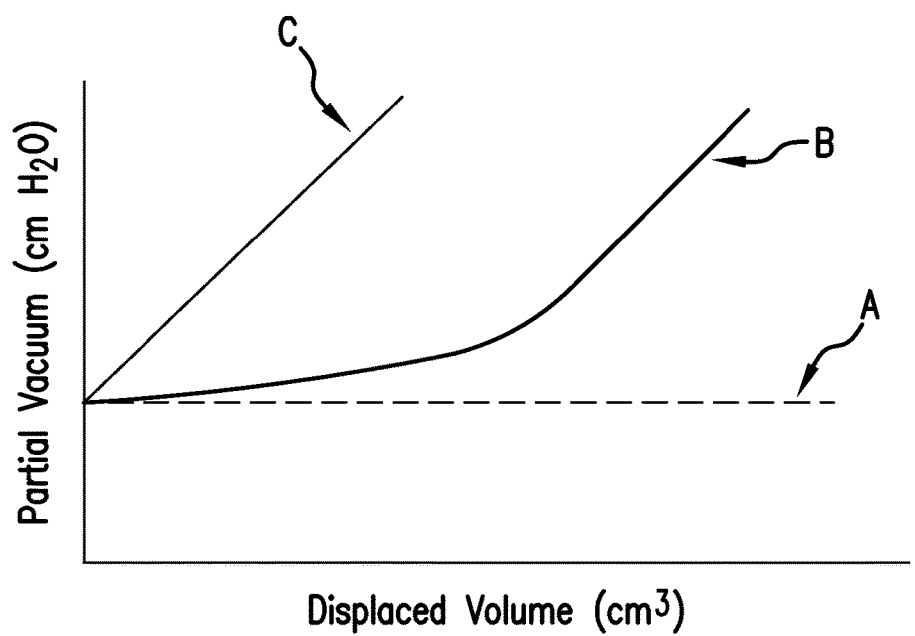
FIG. 12 depicts in graphical form the effect of including a buffering component on partial vacuum changes induced by user movements.

The net result of this buffering is to reduce movement-induced changes in vacuum. This is depicted graphically in FIG. 12. In the absence of a buffering component, the movement-induced change in volume is directly related to a corresponding increase in partial vacuum (line C), while the desired response to such a change in volume is no increase in the partial vacuum (line A). The buffering component dampens this vacuum increase until an inflection point, at which the change in volume exceeds the ability of the buffering component to compensate (line B).

Although it is preferred that the material forming the appliance provide the necessary resiliency, if necessary a metallic or plastic memory-shaped piece can be cast into a portion of the region to further enhance the ability to perform the buffering function. In the case of an appliance formed of a flexible membrane and superstructure, this use of metallic or plastic memory shaped material becomes more important. A portion of the superstructure can be formed that flexes in the same manner as the concave region of the unitary appliance discussed above.

G. Sound Management and Abatement

As the devices described herein are primarily intended for use during sleep, the ability to minimize disruptions due to noise and/or vibrations can provide clear advantages to the user. Many of the pumping technologies available in the art create substantial noise during use. Moreover, when the pump is cycled on and off during the night, the abrupt changes in sound levels can be particularly disruptive to sleep. In certain embodiments therefore, the devices described herein are coupled with devices that provide improved comfort by managing the sound, masking the sound, and/or cancelling the sound produced during use of the therapeutic appliance.

The term "sound management" as used herein refers to reducing the sound level produced by the device. Motors running at high speed tend to be noisy; low speeds tend to be quiet. As discussed above, DC motor speed is typically controlled by pulse width modulation (PWM). Most positive displacement pumps do not impose a constant torque load on the motor as it rotates 360 degrees. Rather, they have an up stroke and down stroke. When running fast this variation in torque gets lost in the rotor inertia and the motor sounds noisy.

But in a DC motor that is externally commutated, the electronics can determine exactly where in the 360 degree rotation the pump/motor is. In preferred embodiments, the controller is used to increase the electrical pulse width during the rotational portion of the pumping stroke, and decrease the pulse width in the remaining portion of the pumping stroke. By mapping the pump-imposed torque profile of the motor and replicating that with pulse width profile, the pump/motor can be made to run slower, resulting in lower noise and vibration.

In certain embodiments, the therapy appliances of the present invention are combined with sound masking electronics to at least partially mask the noise created by the mechanical and electronic components. The term "sound masking" as used herein refers the addition of natural or artificial sound of a different frequency (more commonly though less-accurately known as "white noise" or "pink noise") into an environment to "mask" or cover-up unwanted sound by using auditory masking. Sound masking reduces or eliminates awareness of pre-existing sounds in a given area and can make a work environment more comfortable, while creating speech privacy so workers can be more productive. Sound masking can also be used in the out-of-doors to restore a more natural ambient environment.

Figure 9:
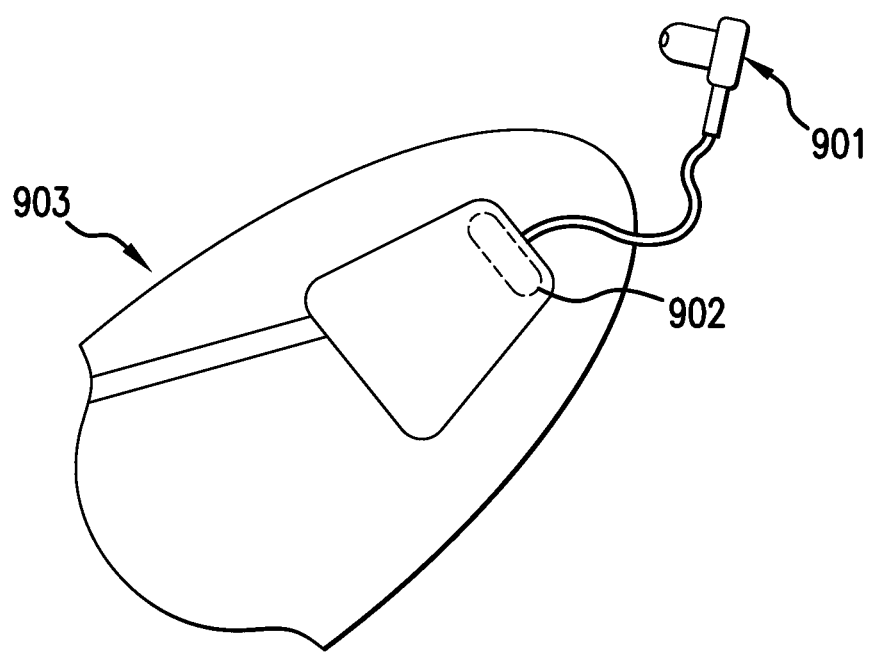
FIG. 9 depicts an exemplary therapy appliance carrying noise cancellation or sound masking electronics and ear buds.

Sound masking is often used in the field of architectural acoustics and in the production of electronic music to mask distracting, undesirable noises. Simple "white noise" machines can be very simple, involving an enclosed fan and (optionally) a speed switch. This fan drives air through small slots in the machine's casing, producing the desired sound. More complex machines may be electronic, and offer a variety of "nature sounds." A Sound generator may be carried on the appliance itself, as depicted in FIG. 9, or may be provided as a separate unit.

Similarly, in certain embodiments, the therapy appliances of the present invention are combined with sound cancelling electronics to at least partially mask the noise created by the mechanical and electronic components. The term "sound cancellation" as used herein refers to the provision of phase cancellation pressure waves. Sound may be considered a pressure wave, which consists of a compression phase and a rarefaction phase. A noise-cancellation speaker emits a sound wave with the same amplitude and the opposite polarity (in antiphase) to the original sound. The waves combine to form a new wave, in a process called interference, and effectively cancel each other out—an effect which is called phase cancellation. Depending on the circumstances and the method used, the resulting sound wave may be so faint as to be inaudible to human ears.

Cyclic sounds, even complex ones, are easier to cancel than random sounds due to the repetition in the wave form. Thus, sound cancellation is particularly applicable to the present invention. In preferred embodiments, a microphone is placed near the ear, and electronic circuitry which generates an "antinoise" sound wave with the opposite polarity of the sound wave arriving at the microphone is delivered through speakers placed at the ear in the form of headphones or earbuds. This results in destructive interference, which cancels out the noise within the enclosed volume of the ear. Noise cancellation circuitry or sound masking circuitry 902 may be carried on the appliance 903 itself, or may be provided as a separate unit. Sound from the circuitry can be provided through small speakers or earbuds 901.

H. Preferred Combinations of the Elements Described Herein

These various elements described above may be provided in various combinations.

A first particularly preferred combination provides a therapy appliance comprising a peripheral surface configured to mate with and thereby enclose an external area of the throat overlying the upper respiratory passage, whereby, when mated, said therapy appliance provides a space-filled chamber lying between the inner surface of the therapy appliance and the throat having an enclosed volume of between 0.5 and 12 in$^3$; and an air pump operably connected to the chamber and configured to maintain a partial vacuum within said chamber at a level between 7.6 cm and 61 cm of water while generating a sound level of less than 40 dB SPL.

A second particularly preferred combination provides a therapy appliance comprising a peripheral surface configured to mate with and thereby enclose an external area of the throat overlying the upper respiratory passage, whereby, when mated, said therapy appliance provides a space-filled chamber lying between the inner surface of the therapy appliance and the throat having an enclosed volume of between 0.5 and 12 in$^3$; and an air pump operably connected to the chamber and configured to maintain a partial vacuum within said chamber, wherein said air pump comprises a positive displacement pump.

A third particularly preferred combination provides a therapy appliance comprising a peripheral surface configured to mate with and thereby enclose an external area of the throat overlying the upper respiratory passage, whereby, when mated, said therapy appliance provides a space-filled chamber lying between the inner surface of the therapy appliance and the throat having an enclosed volume of between 0.5 and 12 in$^3$, wherein said therapy appliance comprises a buffering component configured to dampen swings in the partial vacuum created within the appliance by user movement; and an air pump operatively connected to the space-filled chamber to provide a partial vacuum within the chamber.

A fourth particularly preferred combination provides a therapy appliance comprising a peripheral surface configured to mate with and thereby enclose an external area of the throat overlying the upper respiratory passage, whereby, when mated, said therapy appliance provides a space-filled chamber lying between the inner surface of the therapy appliance and the throat having an enclosed volume of between 0.5 and 12 in$^3$, wherein said peripheral edge is configured to provide a pressure along the contact surface with the user's skin of 60 mm Hg or less at a partial vacuum level within said enclosed volume of between about 7.6 cm to about 61 cm of water; and an air pump operably connected to the chamber and configured to maintain a partial vacuum within said chamber A fifth particularly preferred combination provides a therapy appliance comprising a peripheral surface configured to mate with and thereby enclose an external area of the throat overlying the upper respiratory passage, whereby, when mated, said therapy appliance provides a space-filled chamber lying between the inner surface of the therapy appliance and the throat having an enclosed volume of between 0.5 and 12 in$^3$ and having a leakage rate of air into the space of between 0.005 and 0.5 in$^3$/min; an air pump operably connected to the chamber and configured to maintain a partial vacuum within said chamber, wherein said air pump comprises a positive displacement pump; and a vacuum control module comprising a microcontroller coupled to a vacuum or pressure sensor and motor control circuitry which controls the pump on/off cycles and/or speed.

A sixth particularly preferred combination provides a therapy appliance which is a biocompatible single integral element that provides a seal at the skin interface having a low leakage rate of air into the enclosed chamber, preferably a rate of between 0.005 and 0.5 in$^3$/min, and most preferably at 0.01 and 0.1 in$^3$/min; a diaphragm pump having a single stroke displacement of between 0.001 and 0.01 in$^3$, and most preferably in the range of 0.003 to 0.005 in$^3$, driven using a rotary brushless DC motor or a linear DC motor; and a vacuum control module comprising a microcontroller coupled to a vacuum or pressure sensor and motor control circuitry which controls the pump on/off cycles and/or speed.

A seventh preferred combination comprises any of these first 6 combinations that comprise an air pump, driving motor, control module, and a battery providing power to the driving motor and control module which are wearably supported by the therapy appliance, preferably in a single housing, thereby providing an ambulatory therapy apparatus.

An eighth preferred combination comprises any of the first 7 combinations, where the therapy appliance further comprises a buffering component configured to dampen swings in the partial vacuum created within the appliance by user movements such as swallowing or coughing.

A ninth preferred combination comprises any of the first 8 combinations, where the therapy appliance comprises one or more continuous "ridge lines" between 0.005 and 0.05 inches tall and between 0.005 and 0.05 wide, and most preferably about 0.01 inches tall and 0.01 inches wide in maximal dimension, that run roughly parallel to the periphery of the seal.

A tenth preferred combination comprises any of the first 9 combinations, where the air pump comprises a diaphragm pump having a single stroke displacement of between 0.001 and 0.01 in$^3$, and most preferably in the range of 0.003 to 0.005 in$^3$, driven using a rotary brushless DC motor or a linear DC motor; and optionally includes a vacuum control module comprising a microcontroller coupled to a vacuum or pressure sensor and motor control circuitry which controls the pump on/off cycles and/or speed.

An eleventh preferred combination comprises any of the first 10 combinations, where a vacuum control module is provided that is programmed to operate the air pump in a discontinuous fashion.

A twelfth preferred combination comprises any of the first 11 combinations, where a vacuum control module is provided that is programmed to provide a first pumping mode to generate an initial partial vacuum within the chamber, and a second pumping mode to maintain the partial vacuum within the chamber.

A thirteenth preferred combination comprises any of the first 12 combinations, where the therapy appliance is configured such that when mated to the user and a partial vacuum within said chamber at a level between 7.6 cm and 61 cm of water is produced, the therapy appliance provides a maximal leakage rate of air into the chamber of between 0.005 and 0.5 in$^3$/min.

A fourteenth preferred combination comprises any of the first 13 combinations, where the therapy appliance is configured to provide a peripheral surface that distributes the force load across a sufficient skin area such that no pressure along the contact surface with the user's skin exceeds 60 mm Hg, preferably 40 mm Hg, more preferably 30 mm Hg, and most preferably 25 mm Hg.

A fifteenth preferred combination comprises any of the first 14 combinations where the therapy appliance is configured to provide a peripheral surface that is formed of a material having a durometer of between 15 and 30.

A sixteenth preferred combination comprises any of the first 15 combinations where the therapy appliance comprises a disposable flexible membrane detachably supported by a superstructure providing sufficient support to maintain the chamber under the desired partial vacuum.

A seventeenth preferred combination comprises any of the first 16 combinations where the therapy appliance comprises a buffering component configured to dampen swings in the partial vacuum created within the appliance by user movement.

An eighteenth preferred combination comprises any of the first 17 combinations where the therapy appliance further comprises sound masking and/or sound cancellation electronics.

A nineteenth preferred combination comprises any of the first 18 combinations where the therapy appliance further comprises one or more characteristic sensors, the results of which are used by the controller for control of the apparatus and/or are stored for later access, display, or data transmission from the storage location to an external device. These preferably comprise one or more characteristic sensors that generate an electronic signal indicative of one or more characteristics selected from the group consisting of respiratory cycles, apnea events, snoring events, blood pressure, heart rate and blood oxygen saturation.

A twentieth preferred combination comprises any of the first 19 combinations where the therapy appliance further comprises data transfer electronics for data import and/or export by wired and/or wireless means between the control module and an external device, such as a PDA, computer, cellular telephone, network connection, etc.

A twenty first preferred combination comprises any of the first 20 combinations where the therapy appliance further comprises a strap to maintain position on the user during periods of low vacuum, such as when the partial vacuum is cycled to a lower level during at least part of the therapy period.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

What is claimed:

1. An apparatus for alleviating obstruction of an airway, comprising:
    a therapy appliance comprising a peripheral surface configured to mate with and thereby enclose an external area of the throat overlying the upper respiratory passage, whereby, when mated, said therapy appliance provides a space-filled chamber lying between the inner surface of the therapy appliance and the throat having an enclosed volume of between 0.5 and 12 in$^3$, wherein said peripheral surface is configured to provide a pressure along the contact surface with the user's skin of 60 mm Hg or less at a partial vacuum level within said enclosed volume of between about 7.6 cm to about 61 cm of water;
    an air pump operably connected to the chamber and configured to maintain a partial vacuum within said chamber; and
    a vacuum control module comprising a microcontroller operatively coupled to a vacuum or pressure sensor and motor control circuitry which controls the air pump on/off cycles and/or speed to maintain the partial vacuum level,
    wherein the air pump, driving motor, vacuum control module, and a battery providing power to the driving motor and vacuum control module are wearably supported by the therapy appliance, thereby providing an ambulatory therapy apparatus.

2. An apparatus according to claim 1, wherein said vacuum control module is programmed to operate the air pump in a discontinuous fashion.

3. An apparatus according to claim 1, wherein said vacuum control module is programmed to provide a first pumping mode to generate an initial partial vacuum within the chamber, and a second pumping mode to maintain the partial vacuum.

4. An apparatus according to claim 1, wherein the therapy appliance is configured such that when mated to the user and the partial vacuum within said enclosed volume of between about 7.6 cm and 61 cm of water is produced, the therapy appliance a provides a maximal leakage rate of air into the chamber of between 0.005 and 0.5 in$^3$/min.

5. An apparatus according to claim 1, wherein said peripheral surface is formed of a material having a durometer of between 15 and 30.

6. An apparatus according to claim 1, wherein said peripheral surface comprises one or more continuous ridge lines between 0.005 and 0.05 inches tall and between 0.005 and 0.05 inches wide in their maximal dimension that run approximately parallel to the outer edge of the peripheral surface.

7. An apparatus according to claim 1, wherein said therapy appliance comprises a disposable flexible membrane detachably supported by a superstructure providing sufficient support to maintain said chamber under partial vacuum.

8. An apparatus according to claim 1, wherein said therapy appliance further comprises a buffering component configured to dampen swings in the partial vacuum created within the appliance by user movement.

9. An apparatus according to claim 1, wherein said air pump comprises a diaphragm pump having a single stroke displacement of between 0.001 and 0.01 in$^3$ driven using a rotary brushless DC motor or a linear DC motor.

10. An apparatus according to claim 1, wherein said therapy appliance further comprises sound masking and/or sound cancellation electronics.

11. An apparatus according to claim 1, wherein said therapy appliance further comprises one or more characteristic sensors.

12. An apparatus according to claim 11, wherein said one or more characteristic sensor generate an electronic signal indicative of one or more characteristics selected from the group consisting of respiratory cycles, apnea events, snoring events, blood pressure, heart rate and blood oxygen saturation.

13. An apparatus according to claim 1, wherein said therapy appliance further comprises data transfer electronics for data import and/or export between the therapy appliance and an external device.

14. An apparatus according to claim 1, wherein said therapy appliance further comprises a strap to maintain position on the user during periods of low vacuum.

15. An apparatus according to claim 1, wherein said air pump is a regenerative pump.

16. An apparatus according to claim 1, wherein said peripheral surface comprises a lip for extending across the skin of the user extending outward relative to the space-filled chamber.

17. A method of alleviating obstruction of an airway in a subject, comprising:
   mating a therapy appliance of an apparatus according to claim 1 to an external area of a throat of a subject, thereby creating a space-filled chamber overlying a portion of the upper respiratory passages of the subject; and
   creating a sufficient partial vacuum within the space-filled chamber to move the soft tissues overlying said portion of the upper respiratory passages into the space, thereby increasing the opening of the upper respiratory passages.

18. A method according to claim 17, wherein the obstruction causes sleep apnea or snoring, and said method reduces the number or duration of the apnea or snoring events per hour of sleep by at least 20%.

* * * * *